United States Patent [19]

Yoon

[11] Patent Number: 5,665,100

[45] Date of Patent: Sep. 9, 1997

[54] MULTIFUNCTIONAL INSTRUMENT WITH INTERCHANGEABLE OPERATING UNITS FOR PERFORMING ENDOSCOPIC PROCEDURES

[76] Inventor: InBae Yoon, 2101 Highlands Ridge Dr., Phoenix, Md. 21131

[21] Appl. No.: 376,186

[22] Filed: Jan. 20, 1995

Related U.S. Application Data

[63] Continuation-in-part of Ser. No. 281,814, Jul. 28, 1994, abandoned, which is a continuation of Ser. No. 73,193, Jun. 8, 1993, Pat. No. 5,334,209, which is a continuation of Ser. No. 720,381, Jun. 25, 1991, Pat. No. 5,217,473, which is a division of Ser. No. 446,555, Dec. 5, 1989, Pat. No. 5,026,379.

[51] Int. Cl.$^6$ ............................................. A61B 17/32
[52] U.S. Cl. ........................ 606/170; 606/205; 606/139; 606/144
[58] Field of Search ............................... 606/205–207, 606/151, 170, 142, 144, 139, 147, 148, 167

[56] References Cited

U.S. PATENT DOCUMENTS

| | | |
|---|---|---|
| 2,002,594 | 5/1935 | Wappler et al. . |
| 2,004,559 | 6/1935 | Wappler et al. ........................ 606/46 |
| 2,011,169 | 8/1935 | Wappler ................................ 606/46 |
| 2,028,635 | 1/1936 | Wappler ................................ 606/46 |
| 2,031,682 | 2/1936 | Wappler et al. . |
| 2,032,860 | 3/1936 | Wappler et al. . |
| 2,068,721 | 1/1937 | Wappler et al. . |
| 2,316,297 | 4/1943 | Southerland et al. . |
| 2,518,994 | 8/1950 | Miller . |
| 2,691,370 | 10/1954 | Wallace . |
| 3,827,277 | 8/1974 | Weston . |
| 3,856,016 | 12/1974 | Davis . |
| 3,870,048 | 3/1975 | Yoon . |
| 3,871,379 | 3/1975 | Clarke . |
| 3,911,923 | 10/1975 | Yoon . |
| 3,958,576 | 5/1976 | Komiya . |
| 3,980,086 | 9/1976 | Kletschka et al. . |
| 3,989,049 | 11/1976 | Yoon . |
| 4,049,002 | 9/1977 | Kletschka et al. . |
| 4,085,743 | 4/1978 | Yoon ................................ 128/6 |
| 4,103,680 | 8/1978 | Yoon ................................ 128/6 |
| 4,249,533 | 2/1981 | Komiya . |
| 4,257,420 | 3/1981 | Terayama . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,644,951 | 2/1987 | Bays . |
| 4,662,371 | 5/1987 | Whipple et al. . |

(List continued on next page.)

FOREIGN PATENT DOCUMENTS 2469912  11/1979  France .

*Primary Examiner*—Michael Buiz
*Assistant Examiner*—Mark S. Leonardo

[57] ABSTRACT

An endoscopic instrument includes a forceps unit for being positioned within an anatomical cavity and a removable operating unit. The forceps unit includes a housing, an outer tubular member, an intermediate member, and a handle mechanism coupled with at least one of the intermediate and outer tubular members for creating relative movement between the intermediate and outer tubular members. The outer tubular member has a proximal end mounted by the housing and terminates distally at a distal end. The intermediate member has a tubular body disposed telescopically within the outer tubular member, a proximal end mounted by the housing and an integral one-piece distal end defining a pair of opposed jaws resiliently biased apart such that relative movement of the outer tubular member distal end over the jaws causes the jaws to close. The operating unit includes a hub mounting an inner tubular member removably disposed at least partly within the intermediate member and carrying operating members for performing at least one of the functions of cutting, grasping, manipulating, dissecting, collecting tissue for biopsy, penetrating tissue with a needle, injecting fluids, creating suction, aspirating, irrigating, suturing, ligating, visualizing, illuminating and cauterizing.

66 Claims, 22 Drawing Sheets

U.S. PATENT DOCUMENTS

| | | | |
|---|---|---|---|
| 4,669,470 | 6/1987 | Brandfield . | |
| 4,788,966 | 12/1988 | Yoon . | |
| 4,869,268 | 9/1989 | Yoon . | |
| 4,935,027 | 6/1990 | Yoon . | |
| 4,949,717 | 8/1990 | Shaw . | |
| 4,985,030 | 1/1991 | Melzer et al. . | |
| 4,990,152 | 2/1991 | Yoon . | |
| 5,015,249 | 5/1991 | Nakao et al. . | |
| 5,049,153 | 9/1991 | Nakao et al. | 606/151 |
| 5,099,827 | 3/1992 | Melzer et al. . | |
| 5,100,418 | 3/1992 | Yoon et al. | 606/139 |
| 5,147,356 | 9/1992 | Bhatta . | |
| 5,147,357 | 9/1992 | Rose et al. . | |
| 5,152,780 | 10/1992 | Honkanen et al. . | |
| 5,156,608 | 10/1992 | Troidl et al. . | |
| 5,156,609 | 10/1992 | Nakao et al. . | |
| 5,170,800 | 12/1992 | Smith et al. . | |
| 5,171,250 | 12/1992 | Yoon . | |
| 5,171,258 | 12/1992 | Bales et al. . | |
| 5,172,700 | 12/1992 | Bencini et al. . | |
| 5,176,695 | 1/1993 | Dulebohn . | |
| 5,176,700 | 1/1993 | Brown et al. . | |
| 5,192,298 | 3/1993 | Smith et al. . | |
| 5,196,023 | 3/1993 | Martin . | |
| 5,203,785 | 4/1993 | Slater . | |
| 5,211,655 | 5/1993 | Hasson . | |
| 5,217,030 | 6/1993 | Yoon . | |
| 5,217,460 | 6/1993 | Knoepfler . | |
| 5,219,354 | 6/1993 | Choudhury et al. . | |
| 5,220,928 | 6/1993 | Oddsen et al. . | |
| 5,222,961 | 6/1993 | Nakao et al. . | |
| 5,222,962 | 6/1993 | Burkhart . | |
| 5,222,976 | 6/1993 | Yoon . | |
| 5,226,908 | 7/1993 | Yoon . | |
| 5,300,087 | 4/1994 | Knoepfler . | |
| 5,318,589 | 6/1994 | Lichtman . | |
| 5,334,199 | 8/1994 | Yoon . | |
| 5,342,381 | 8/1994 | Tidemand . | |
| 5,342,389 | 8/1994 | Haber et al. . | |
| 5,342,390 | 8/1994 | Slater et al. . | |
| 5,366,459 | 11/1994 | Yoon . | |

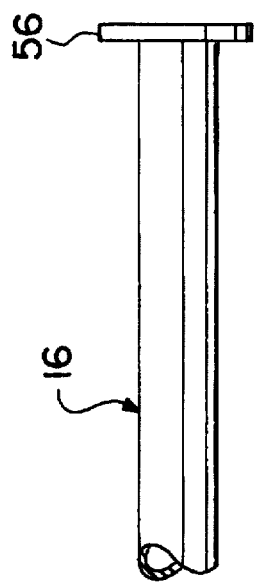
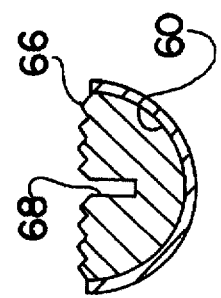
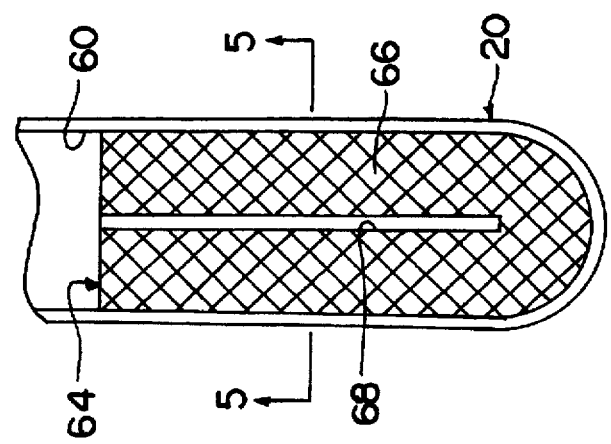
FIG. 3
FIG. 5
FIG. 4

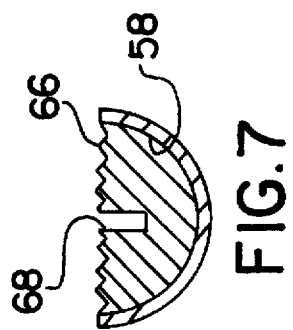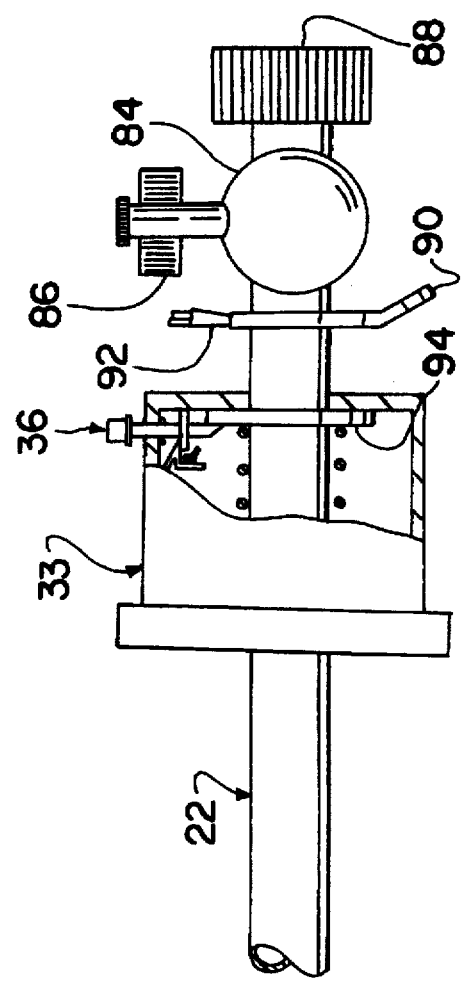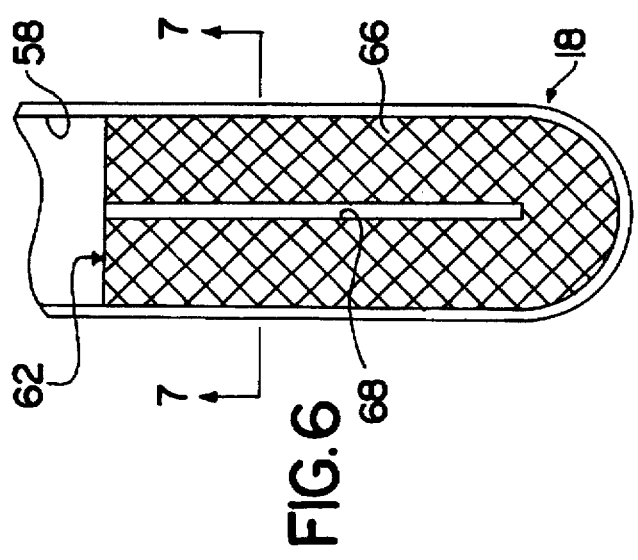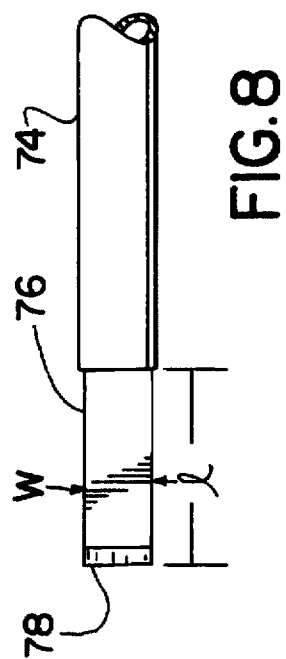

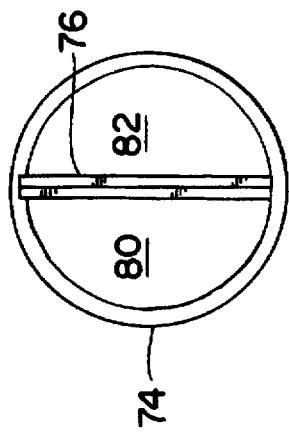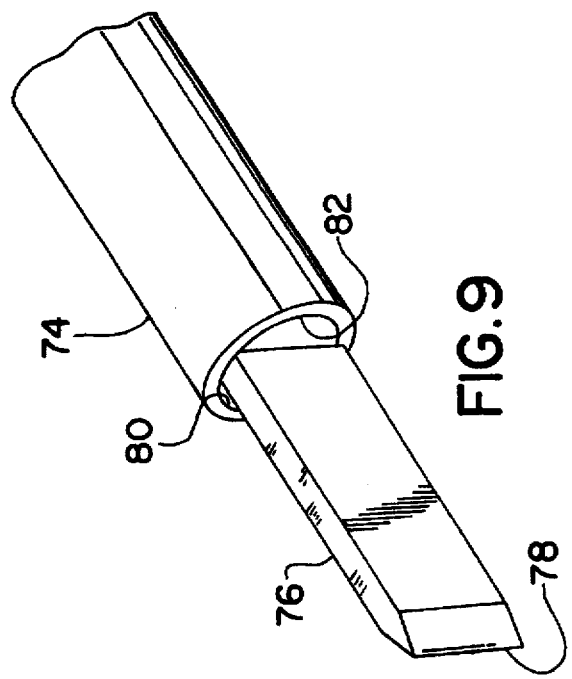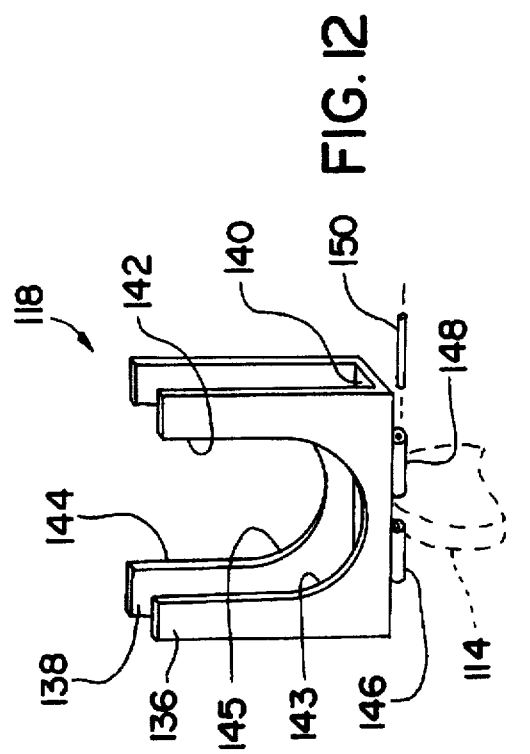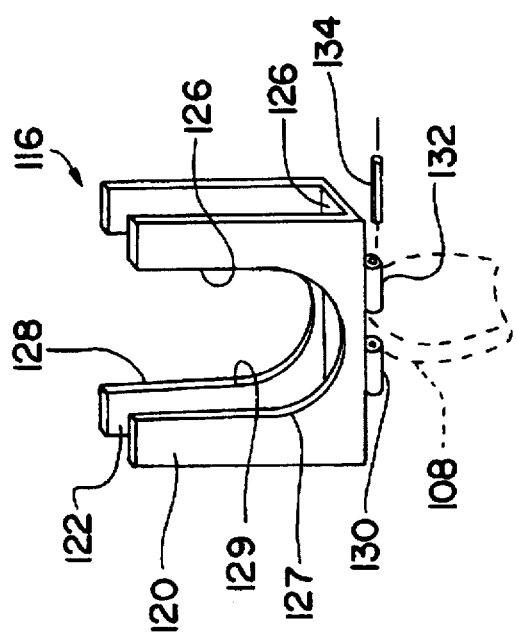

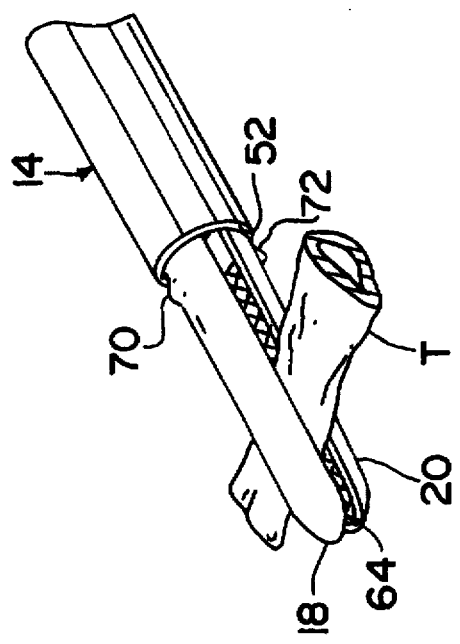
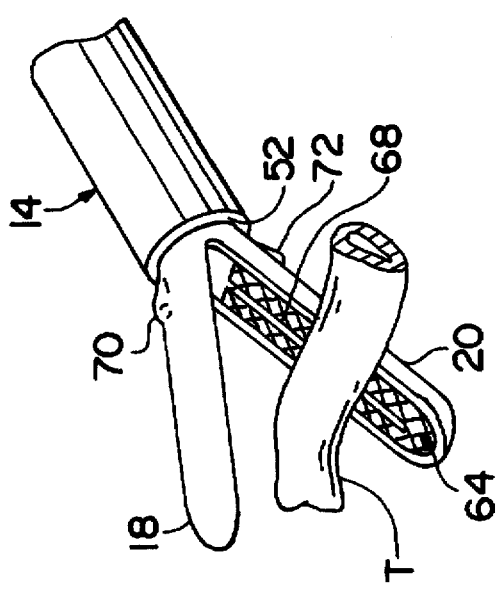
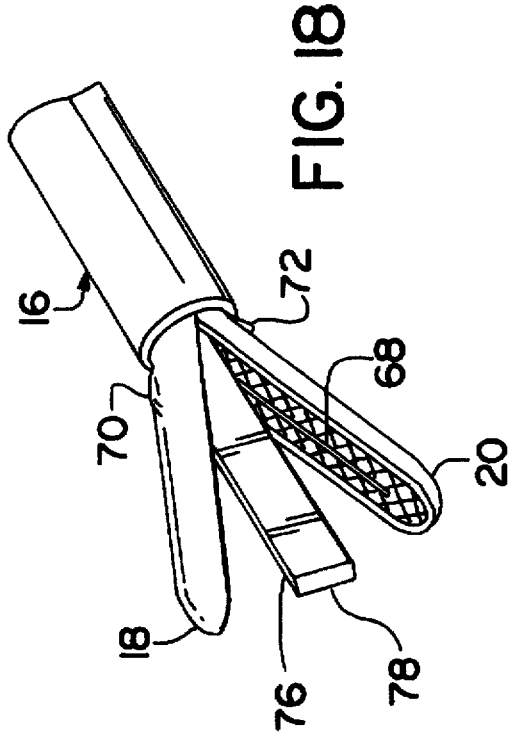

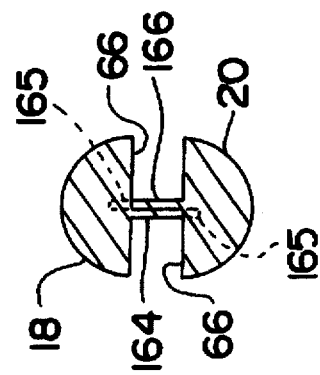
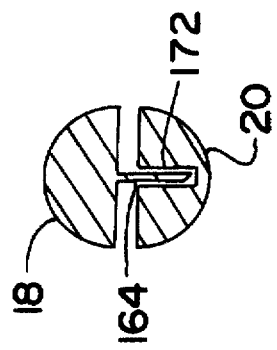
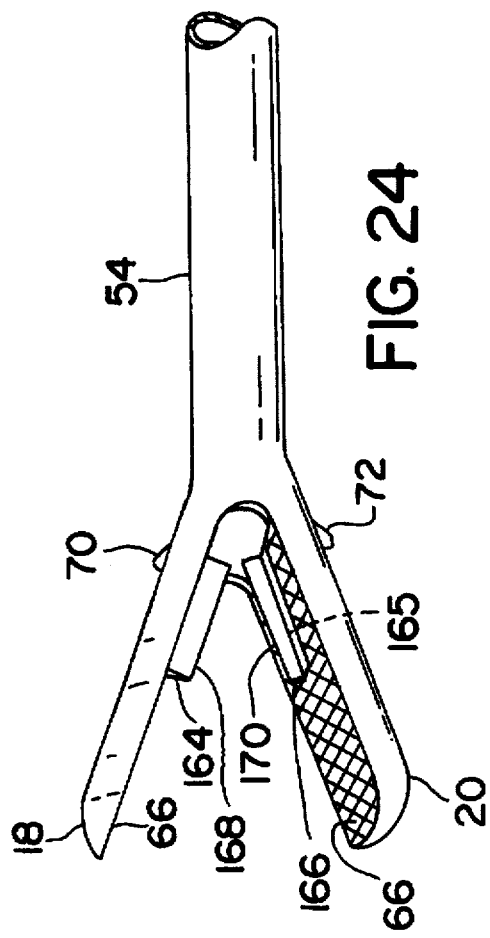
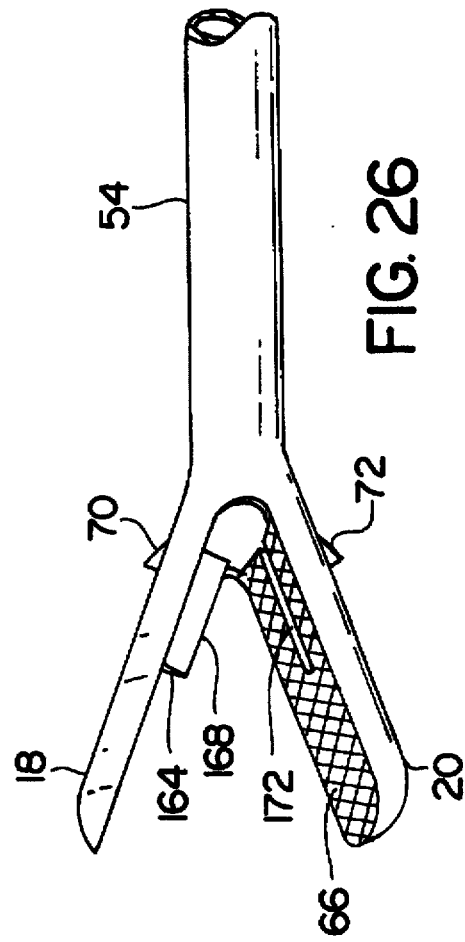

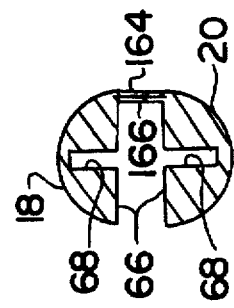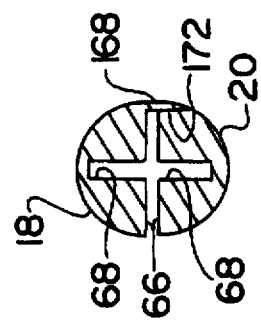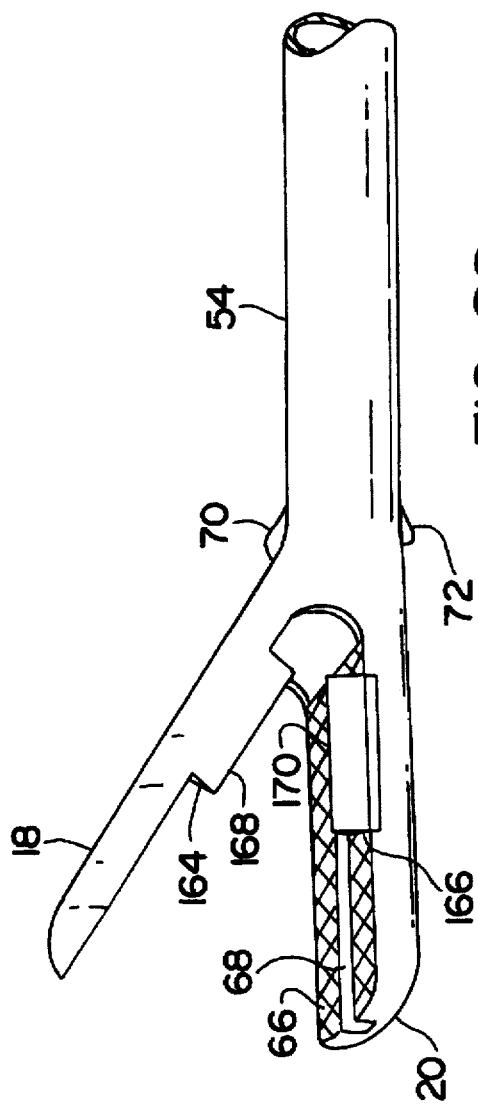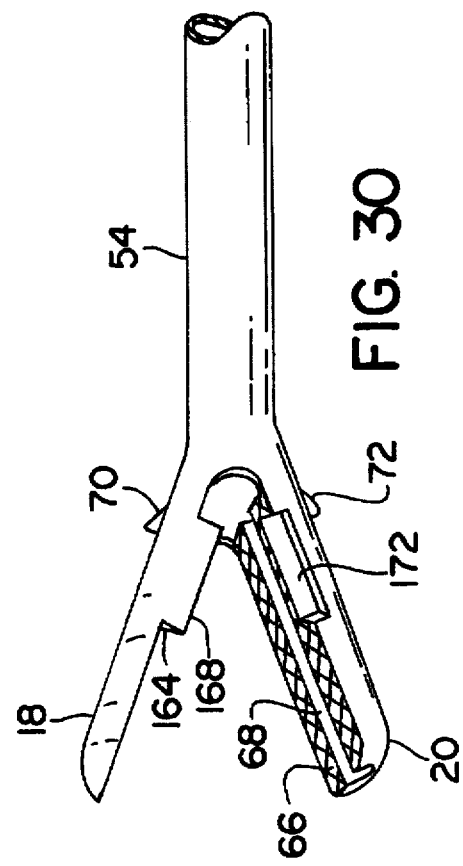

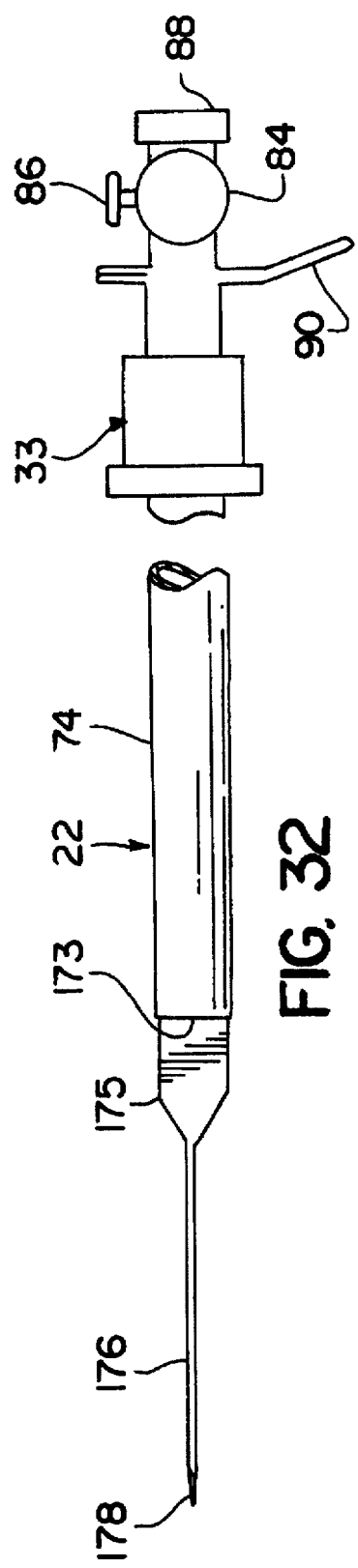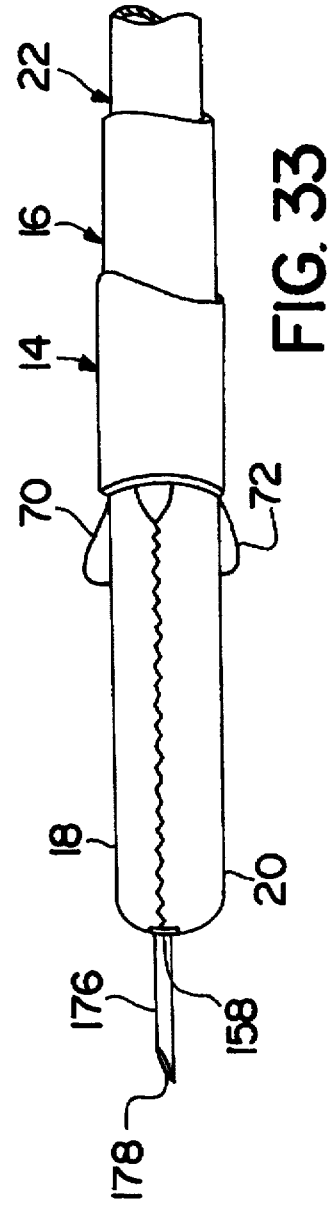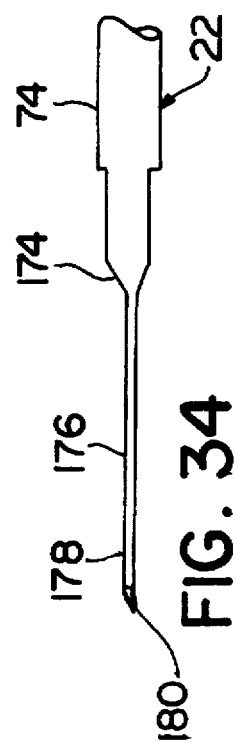
FIG. 32
FIG. 33
FIG. 34

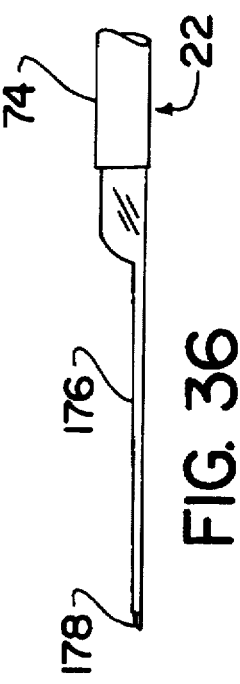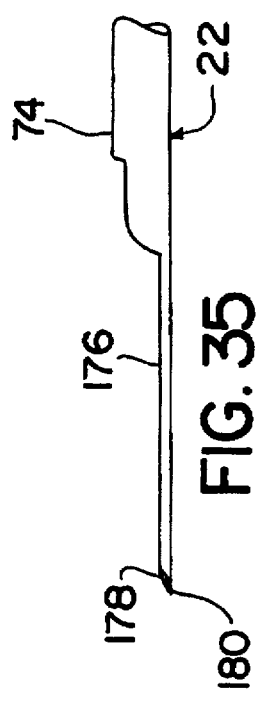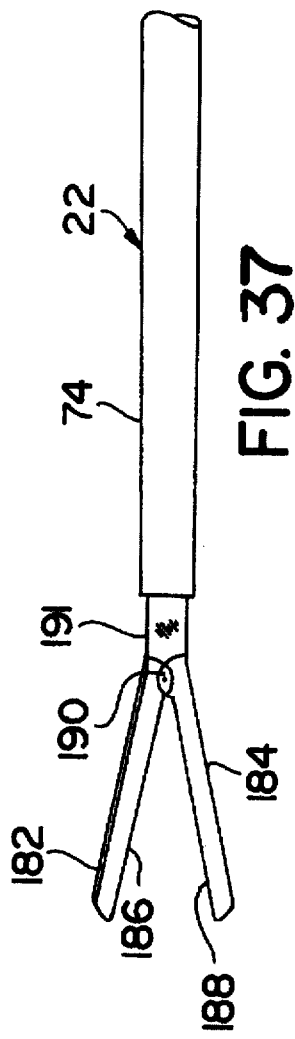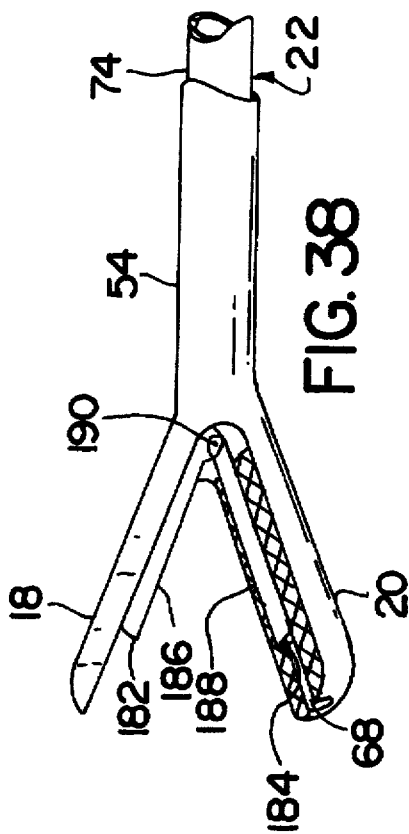
FIG. 36
FIG. 35
FIG. 37
FIG. 38

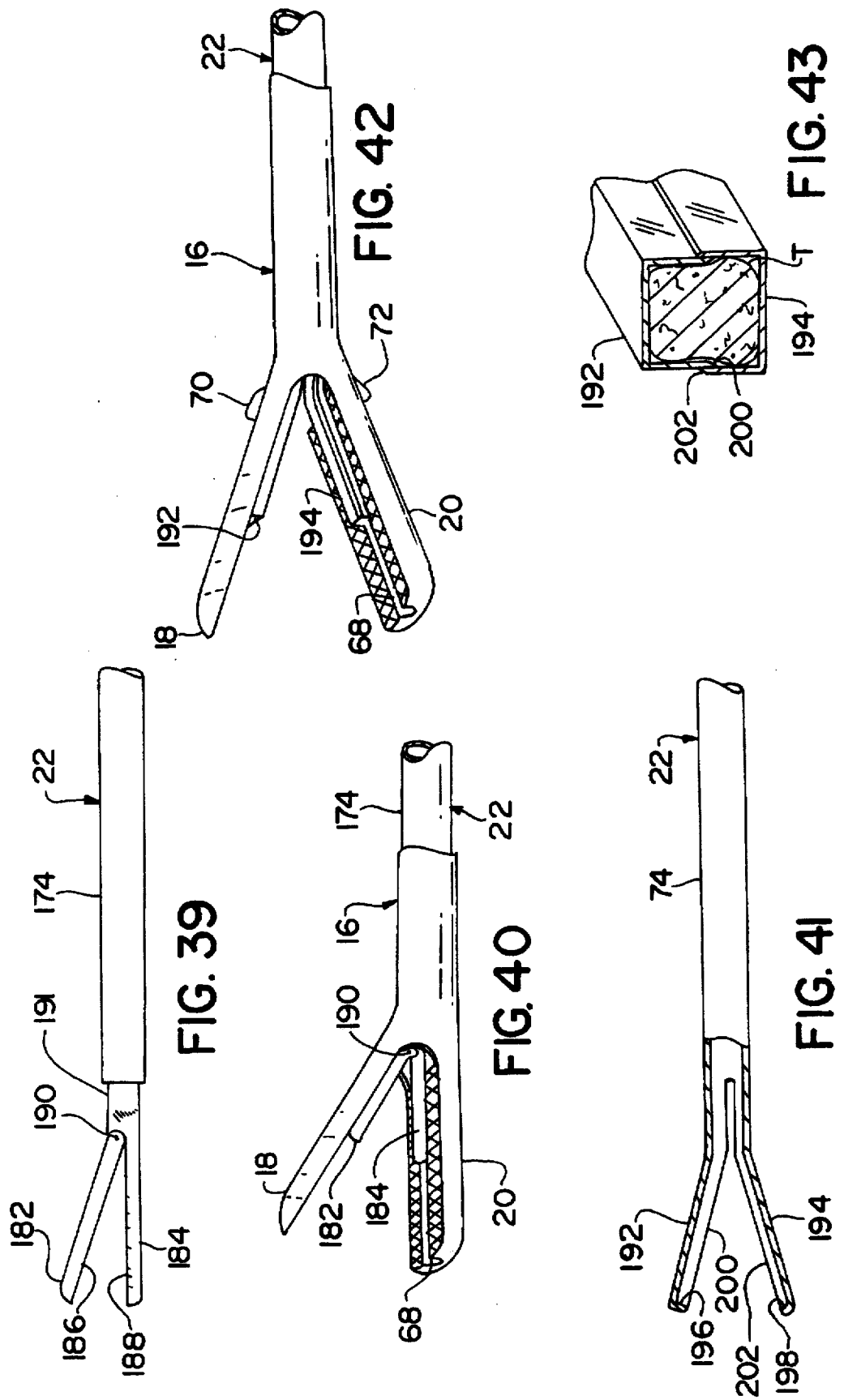

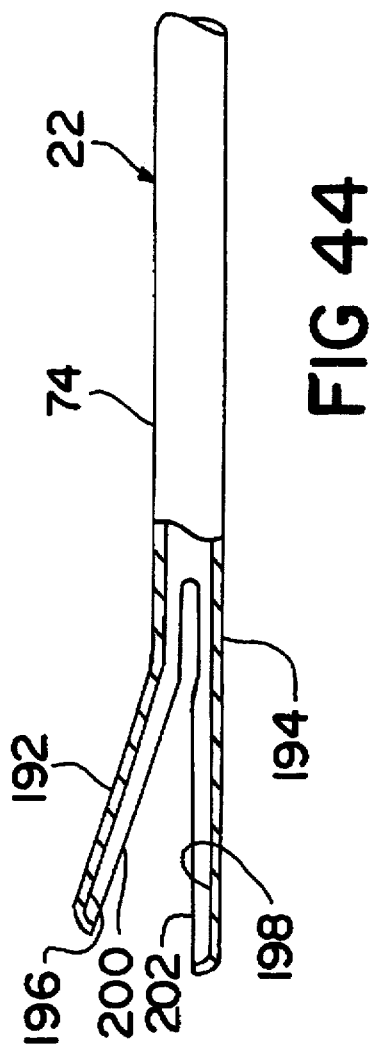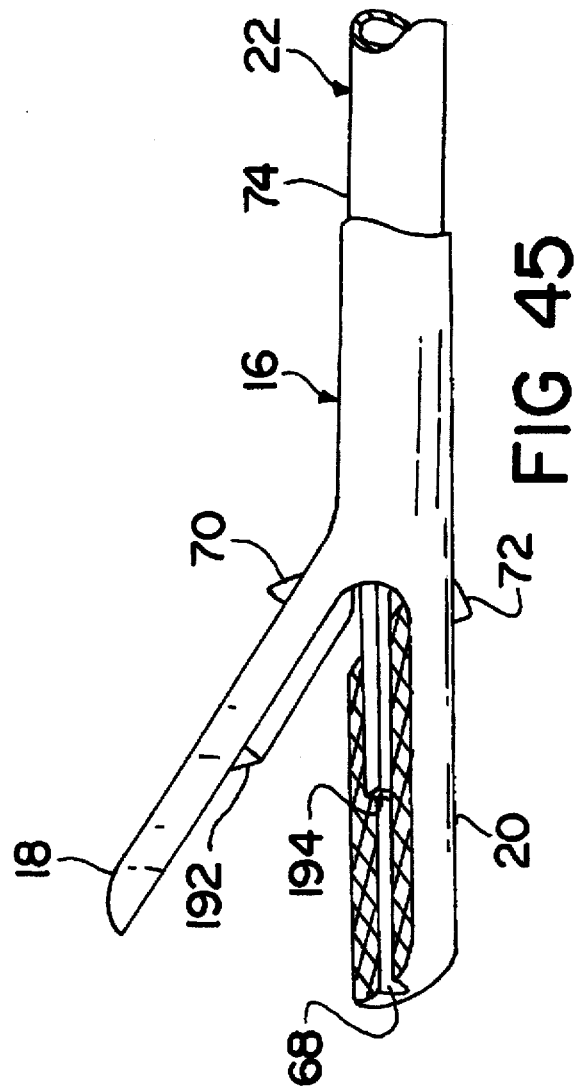

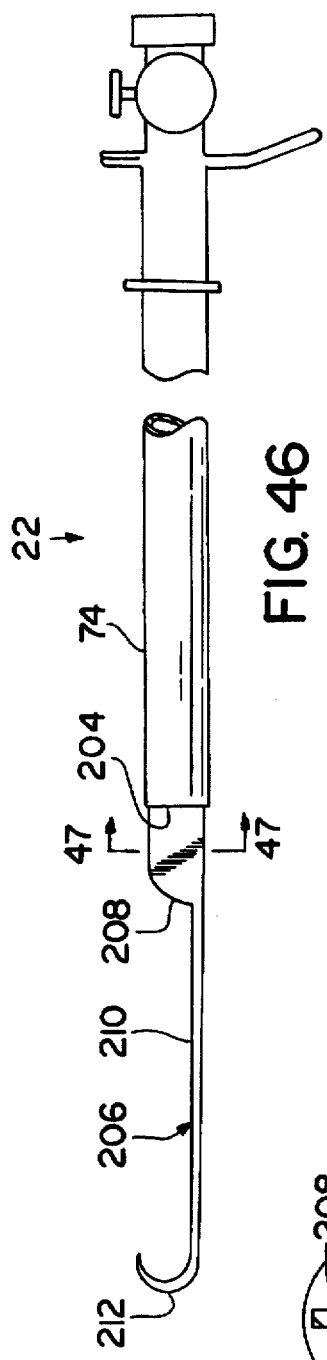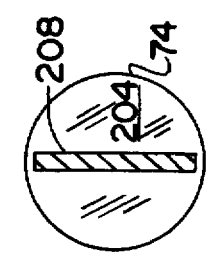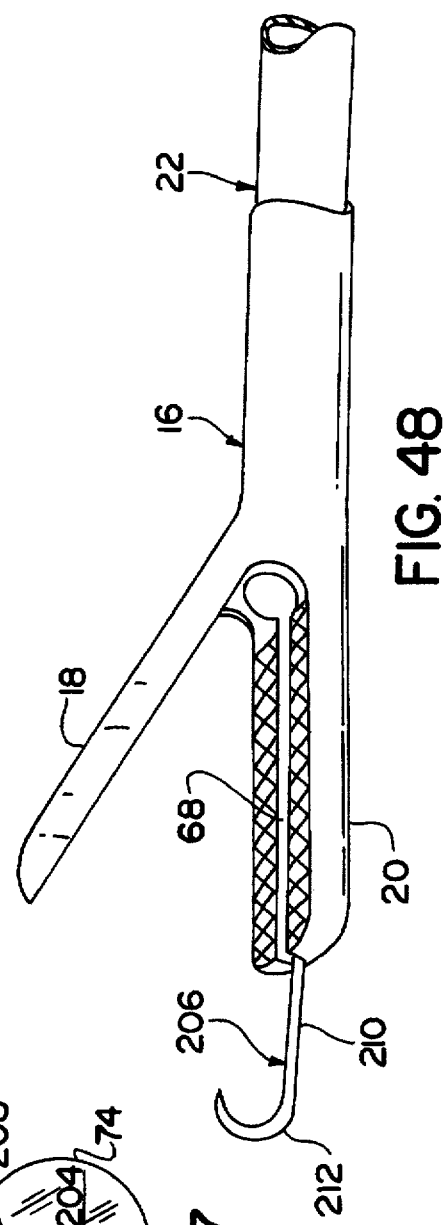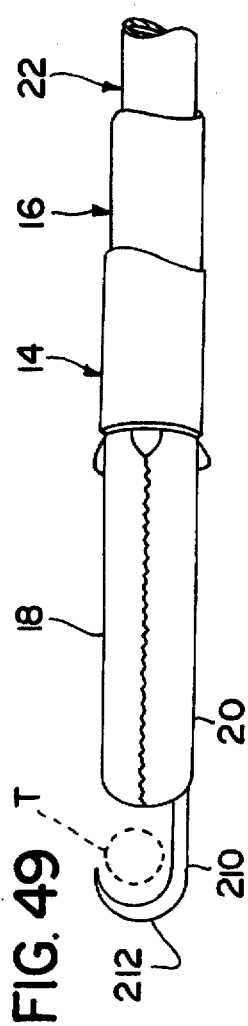
FIG. 46
FIG. 47
FIG. 48
FIG. 49

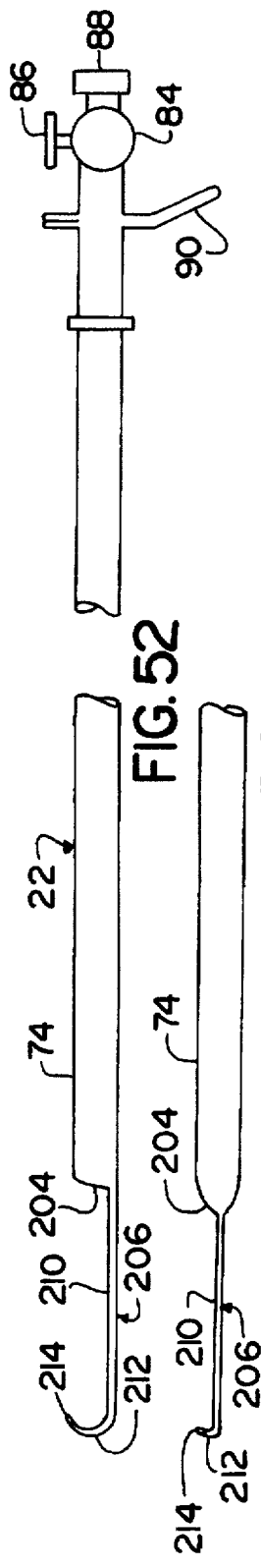
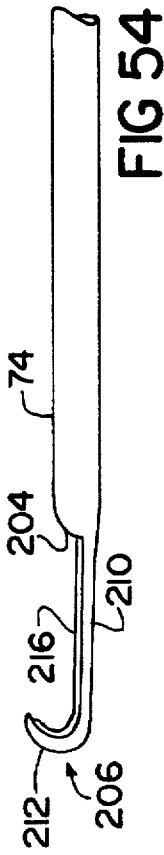
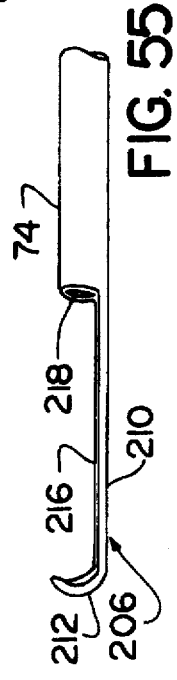
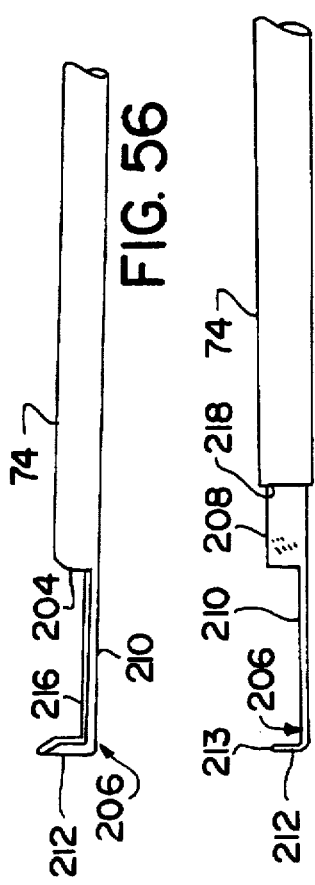
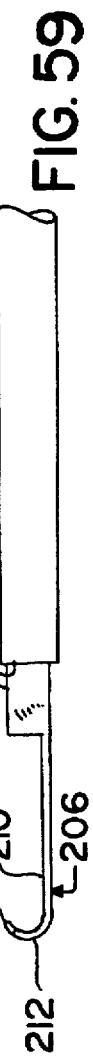
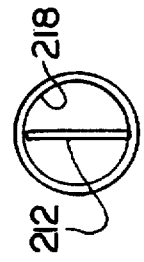
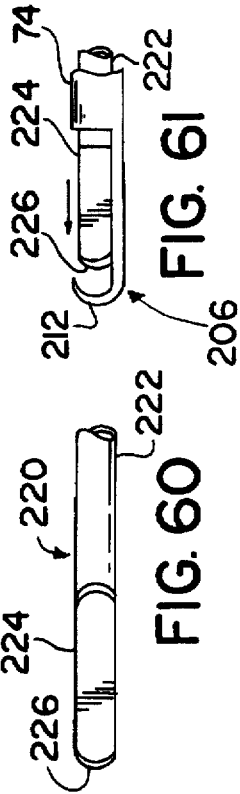
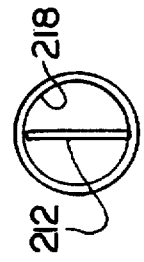

MULTIFUNCTIONAL INSTRUMENT WITH INTERCHANGEABLE OPERATING UNITS FOR PERFORMING ENDOSCOPIC PROCEDURES

CROSS-REFERENCE TO RELATED APPLICATIONS

This application is a continuation-in-part of applicant's patent application Ser. No. 08/281,814, filed Jul. 28, 1994, now abandoned which is a continuation of patent application Ser. No. 08/073,193, filed Jun. 8, 1993, now U.S. Pat. No. 5,334,209, which was a continuation of patent application Ser. No. 07/720,381, filed Jun. 25, 1991, now U.S. Pat. No. 5,217,473, which was a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention:

The present invention relates generally to medical procedures and instruments and, more particularly, to a multifunctional instrument with interchangeable operating units for performing endoscopic procedures.

2. Discussion of the Prior Art:

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

SUMMARY OF THE INVENTION

Accordingly, it is a primary object of the present invention to overcome the above mentioned disadvantages of the prior art with an endoscopic instrument capable of performing multiple functions.

Another object of the present invention is to minimize the number of incisions required for performing an endoscopic procedure by performing multiple functions through a single incision with an endoscopic instrument having a forceps unit for performing grasping functions and interchangeable operating units for performing at least one of the functions of grasping, cutting, dissecting, aspirating, irrigating, penetrating, injecting, creating suction, collecting biopsy samples, hooking, manipulating and cauterizing through the forceps unit.

A further object of the present invention is to reduce the need for frequent substitution of instruments through a single incision by carrying out multiple functions with a single endoscopic instrument having a forceps unit that remains within an anatomical cavity and interchangeable operating units for performing at least one of the functions of grasping, cutting, dissecting, aspirating, irrigating, penetrating, injecting, creating suction, collecting biopsy samples, hooking, manipulating and cauterizing through the forceps unit.

It is another object of the present invention to bias jaws of an endoscopic instrument together to ensure smooth entry of the endoscopic instrument through a portal sleeve and to prevent inadvertent snagging of anatomical tissue.

Some of the advantages of the present invention over the prior art are that the endoscopic instrument can perform multiple functions through a single incision thereby minimizing the number of incisions required to perform an endoscopic procedure, that the frequency of substitution of instruments through a single incision can be reduced, that use of an endoscopic instrument for picking-up and holding objects is simplified, that objects can be held without the need for exerting continuous hand or finger pressure, that single-handed operation of a forceps unit and an operating unit is facilitated, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity and a removable operating unit. The forceps unit includes a housing, an outer tubular member, an intermediate member, and a handle mechanism coupled with at least one of the intermediate and outer tubular members for creating relative movement therebetween. The outer tubular member has a proximal end mounted by the housing and terminates distally at a distal end. The intermediate member has a tubular body disposed telescopically within the outer tubular member, a proximal end mounted by the housing and an integral one-piece distal end defining a pair of opposed jaws resiliently biased apart such that relative movement of the outer tubular member distal end over the jaws causes the jaws to close. The operating unit includes a hub mounting an inner member removably disposed at least partly within the intermediate member and carrying operating means for performing at least one of the functions of cutting, grasping, hooking, manipulating, dissecting, collecting tissue for biopsy, penetrating, injecting, creating suction, aspirating, irrigating and cauterizing.

Another aspect of the present invention is generally characterized in an endoscopic instrument including a housing, an outer tubular member having a proximal end mounted by the housing and terminating distally at a distal end, an intermediate member having a tubular body disposed telescopically within the outer tubular member, a proximal end mounted by the housing and an integral one-piece distal end defining a pair of opposed jaws resiliently biased apart, the intermediate member defining a lumen in communication with an opening in the housing, bias means for biasing the outer tubular member over the jaws, and handle means coupled with at least one of the intermediate and outer tubular members for creating relative movement between the intermediate and outer tubular members, whereby the pair of opposed jaws can be opened when the distal end of the outer tubular member is moved proximally relative to the jaws.

A further aspect of the present invention is generally characterized in a method of performing an endoscopic procedure including the steps of introducing a tubular member with integral one-piece jaws through an opening in an anatomical cavity wall, grasping anatomical tissue with the jaws, advancing an inner member distally through the tubular member, and performing a medical procedure involving at least one of the functions of cutting, grasping, dissecting, cauterizing, penetrating, injecting, hooking, manipulating, collecting a biopsy, irrigating and aspirating with the inner member.

Yet another aspect of the present invention is generally characterized in a method of performing endoscopic procedures including the steps of introducing a tubular member with integrally formed jaws through an opening in an anatomical cavity wall, advancing an inner member carrying an operating member distally through the tubular member until the operating member protrudes distally from the jaws and performing a medical procedure with the operating member.

An additional aspect of the present invention is generally characterized in a method of performing endoscopic procedures including the steps of introducing a tubular member with integrally formed jaws through an opening in an anatomical cavity wall, advancing an inner member distally through the tubular member until an operating member having opposed distal portions biased apart is disposed between the jaws, opening the jaws to permit the opposed distal portions of the operating member to separate, positioning anatomical tissue between the opposed distal portions of the operating member, and closing the jaws to move the opposed distal portions of the operating member toward one another.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 is a broken side view of an intermediate member for the endoscopic instrument of FIGS. 1 and 2.

FIG. 4 is a plan view of a lower jaw of the intermediate member shown in FIG. 3.

FIG. 5 is a cross-sectional view of the lower jaw of FIG. 4 taken along line 5—5.

FIG. 6 is a plan view of an upper jaw of the intermediate member shown in FIG. 3.

FIG. 7 is a cross-sectional view of the upper jaw of FIG. 6 taken along line 7—7.

FIG. 8 is a broken side view, partly in section, of an operating unit for the endoscopic instrument of FIGS. 1 and 2.

FIG. 9 is a fragmentary perspective view of the distal end of the operating unit of FIG. 8.

FIG. 10 is frontal view of the operating unit of FIG. 8.

FIGS. 11 and 12 are perspective views of brackets for use in the endoscopic instrument of the present invention.

FIGS. 15 and 16 are fragmentary perspective views of the distal end of the endoscopic instrument of the present invention grasping anatomical tissue.

FIG. 18 is a fragmentary perspective view of the distal end of an endoscopic instrument according to the present invention with jaws open and the inner member advanced distally.

FIG. 24 is a fragmentary perspective view of a modified jaw configuration for use with the endoscopic instrument of the present invention.

FIG. 25 is a cross-sectional view of the jaws of FIG. 24 in a closed condition.

FIG. 26 is a fragmentary perspective view of another modified jaw configuration for use with the endoscopic instrument of the present invention.

FIG. 27 is a cross-sectional view of the jaws of FIG. 26 in a closed condition.

FIG. 28 is a fragmentary perspective view of yet another modified jaw configuration for use with the endoscopic instrument of the present invention.

FIG. 29 is a cross-sectional view of the jaws of FIG. 28 in a closed condition.

FIG. 30 is a fragmentary perspective view of still another modified jaw configuration for use with the endoscopic instrument of the present invention.

FIG. 31 is a cross-sectional view of the jaws of FIG. 30 in a closed condition.

FIG. 32 is a side view, broken longitudinally, of a modified inner member carrying a needle.

FIG. 33 is a side view of the needle of FIG. 32 protruding distally from closed forceps jaws.

FIG. 34 is a fragmentary side view of another modified inner member carrying a needle.

FIG. 35 is a fragmentary side view of yet another modified inner member carrying a needle.

FIG. 36 is a fragmentary side view of still another modified inner member carrying a needle.

FIG. 37 is a fragmentary side view of another modified inner member carrying scissors.

FIG. 38 is a fragmentary side view of the scissors of FIG. 37 within jaws of the endoscopic instrument of the present invention.

FIG. 39 is a fragmentary side view of yet another modified inner member carrying scissors.

FIG. 40 is a fragmentary side view of the scissors of FIG. 39 within jaws of the endoscopic instrument of the present invention.

FIG. 41 is a fragmentary side view of still another modified inner member carrying opposed biopsy box members.

FIG. 42 is a fragmentary side view of the biopsy box members of FIG. 41 within jaws of the endoscopic instrument of the present invention.

FIG. 43 is a perspective view, in cross-section, of the biopsy box members of FIG. 41 enclosing a tissue sample.

FIG. 44 is a fragmentary side view of another modified inner member carrying opposed biopsy box members.

FIG. 45 is a fragmentary side view of the biopsy box members of FIG. 44 within jaws of the endoscopic instrument of the present invention.

FIG. 46 is a side view, broken longitudinally, of an alternative inner member carrying a hook for use with the endoscopic instrument of the present invention.

FIG. 47 is a cross-sectional view taken through line 47—47 in FIG. 46.

FIG. 48 is a fragmentary perspective view of the hook of FIG. 46 within jaws of an endoscopic instrument according to the present invention.

FIG. 49 is a fragmentary side view of the hook of FIG. 46 protruding distally from closed jaws.

FIGS. 52–59 are views of other modified inner members for use with the endoscopic instrument of the present invention.

FIGS. 60 and 61 are side views of a cutting member and the cutting member being advanced distally within the inner member shown in FIG. 55.

DESCRIPTION OF THE PREFERRED EMBODIMENTS

The endoscopic instrument of the present invention can be utilized in any type of anatomical cavity; and, accordingly, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
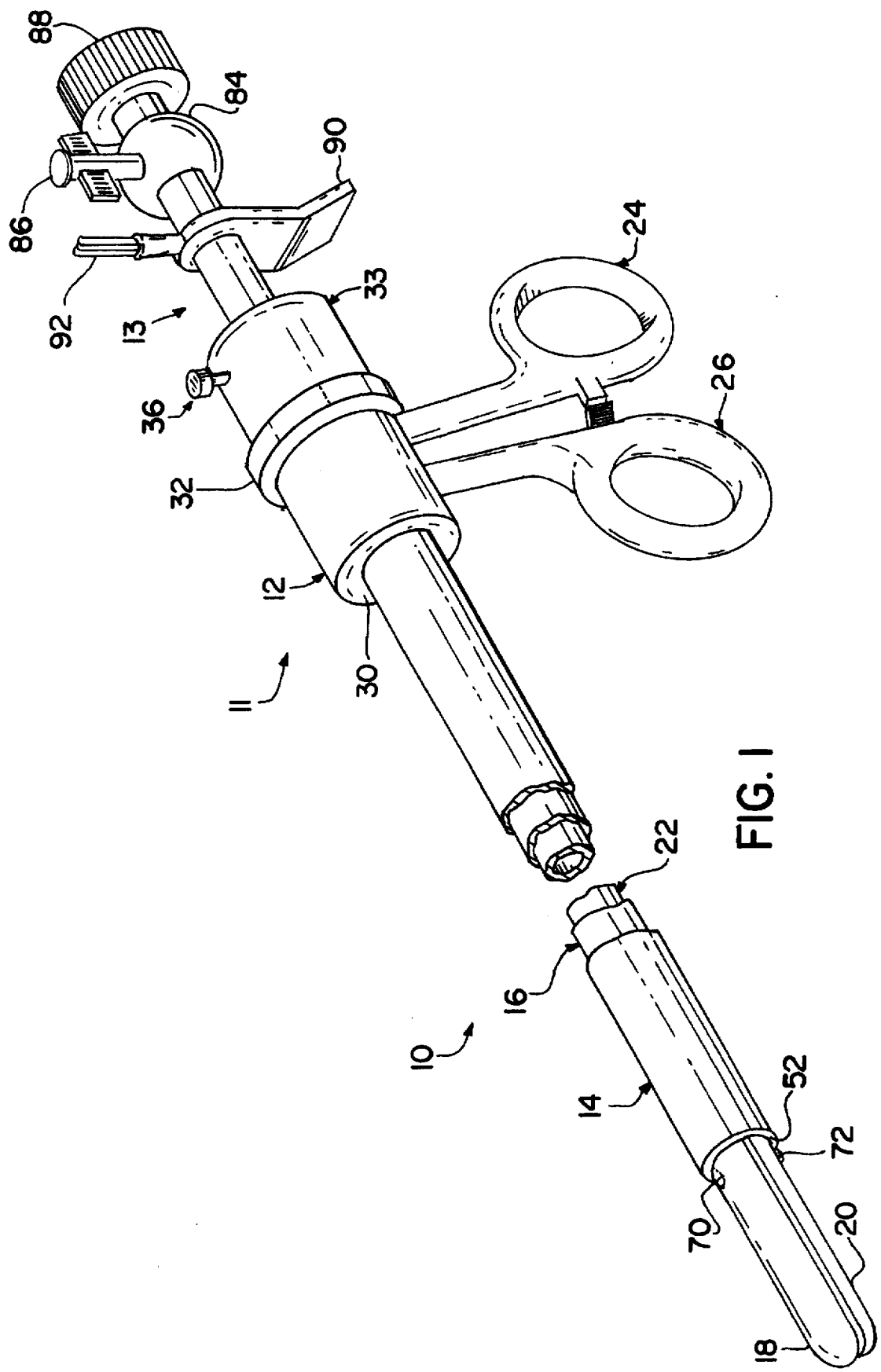
FIG. 1 is a perspective view, broken longitudinally, of an endoscopic instrument according to the present invention.
Figure 2:
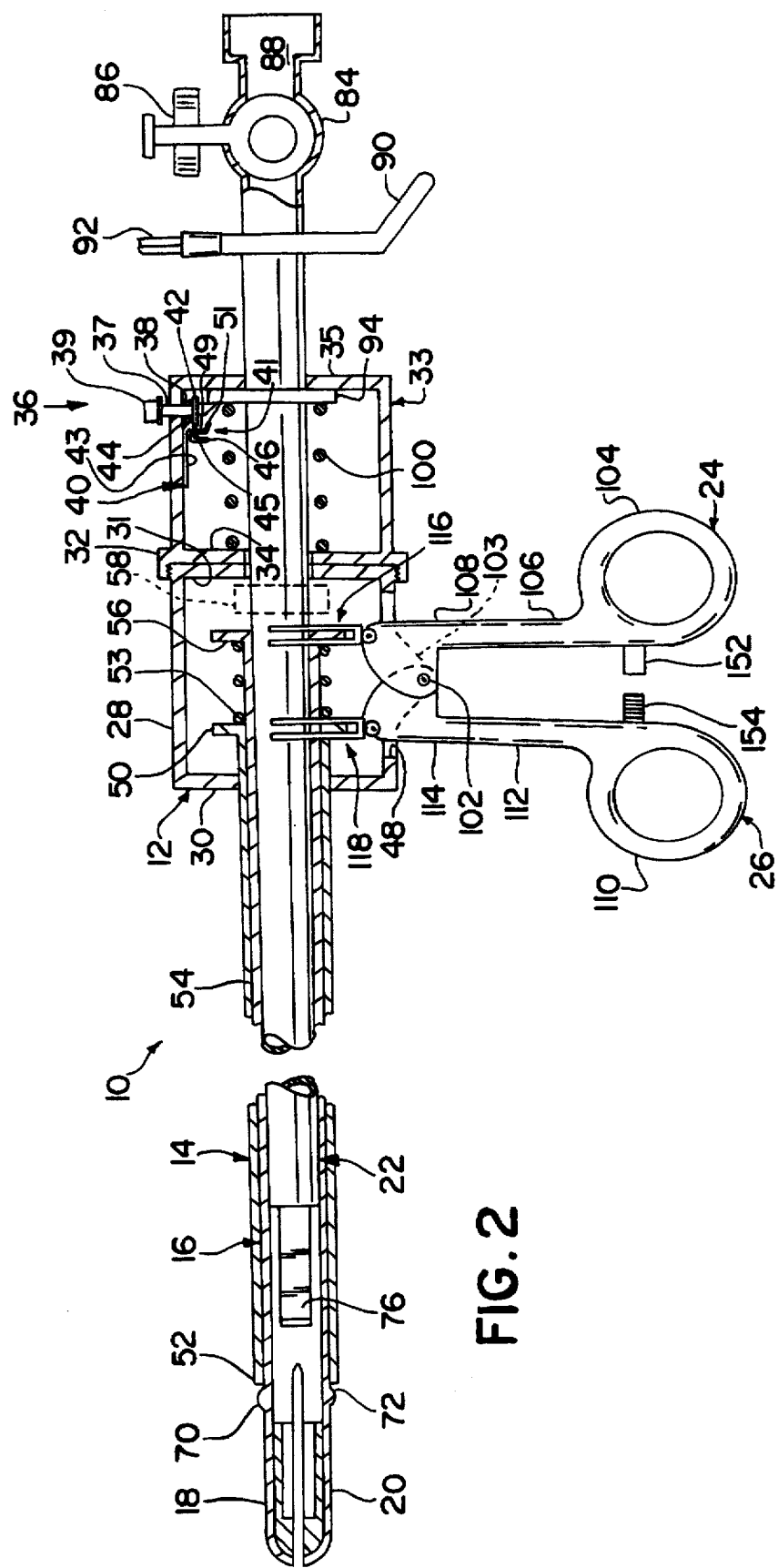
FIG. 2 is a side view, partly in section, of the endoscopic instrument of FIG. 1.

An endoscopic instrument 10 according to the present invention, as shown in FIGS. 1 and 2, includes a forceps unit 11 and an operating unit 13. Forceps unit 11 includes a housing 12, an outer tubular member 14 extending distally from the housing 12, an intermediate tubular member 16 telescopically fitted within the outer tubular member 14 and terminating distally in a pair of opposed jaws 18 and 20, and a pair of handles 24 and 26 extending from the housing at an angle relative to the longitudinal axis of the instrument. Operating unit 13 includes a hub 33 releasably coupled with the housing 12 and carrying an inner member 22 at least partly telescopically fitted within the intermediate tubular member 16.

As best seen in FIG. 2, housing 12 is generally tubular with a cylindrical sidewall 28 and front and rear walls 30 and 31 closing opposite ends of the cylindrical sidewall 28. A rear portion of the cylindrical sidewall 28 is externally threaded to mate with an internally threaded ring 32 carried by the cylindrical hub 33. Hub 33 has front and rear endcaps 34 and 35 and can be mated with or separated from housing 12 by rotation; and when mated with housing 12, the front endcap 34 abuts or is proximate housing rear wall 31. A slotted opening 48 is formed in the cylindrical sidewall 28 of housing 12 and extends longitudinally between the front and rear walls 30 and 31 of the housing to permit handles 24 and 26 to pass therethrough.

Outer tubular member 14 is open at both ends and extends through an opening in the housing front wall 30 to terminate proximally at a transverse flange 50 disposed between front wall 30 and rear wall 31 of the housing. Distal end 52 of outer tubular member 14 can be blunt as shown, tapered, beveled or chamfered as desired or have any other suitable distal configuration. Preferably, outer tubular member 14 is made of a substantially cylindrical length of a substantially rigid material, such as stainless steel or other medically acceptable plastic or metal material.

Intermediate member 16 includes a tubular body 54 telescopically fitted within the outer tubular member 14. The tubular body 54 terminates proximally at a transverse flange 56 disposed within housing 12 between the outer tubular member flange 50 and housing rear wall 31; and, as best seen in FIGS. 3–7, a distal end of tubular body 54 is split longitudinally to form integral one-piece jaws 18 and 20 in opposed relation. Jaws 18 and 20 are normally biased apart as shown and define opposed semicylindrical recesses 58 and 60 for carrying jaw inserts 62 and 64. Jaw inserts 62 and 64 can be permanently or removably secured within the semicylindrical recesses using adhesives, detents, or any other suitable method of attachment or can be formed with jaws 18 and 20 as an integral one-piece construction. Each insert defines a grasping surface or tread 66 suitable for grasping anatomical tissue or holding instruments such as a needle and a longitudinal slot or groove 68 extending from a proximal end of the insert to a position proximally spaced from the distal end of the insert. A repeated pattern of diamond-shaped protrusions is shown for tread 66; however, other surfaces such as those having parallel ribs or textured portions could be used. The depth of each groove 68 will depend on the size of any operating members carried by the inner member 22 as will be described in more detail below. Wedge-like cams 70 and 72 are formed on respective exterior surfaces of jaws 18 and 20 and are distally spaced from outer member distal end 52 when jaws 18 and 20 are open. Cams 70 and 72 taper toward the joint region or junction where each jaw connects with the tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing the upper and lower jaws 18 and 20 apart while permitting the jaws to be moved towards one another in response to axial forces acting on the jaws and/or cams as a result of relative movement between the outer tubular member 14 and intermediate member 16. Referring again to FIG. 2, it can be seen that a bias member 53 is connected between the outer member flange 50 and the intermediate member flange 56 such that the outer tubular member 14 is normally biased distally relative to the intermediate member causing the distal end 52 of the outer member to slide over the jaws 18 and 20 so that the jaws are normally closed together as shown in FIGS. 1 and 2. Bias member 53 is shown as a helical coil spring disposed around the intermediate member 16 and held in compression between the outer and intermediate member flanges 50 and 56; however, it will be appreciated that bias member 53 can include various other types of springs as well as other types of bias devices including tension springs, torsion springs, pan springs, leaf springs, rubber, plastic or magnets, for example.

As best seen in FIGS. 8–10, inner member 22 includes a cylindrical or tubular shaft 74 and an operating member in the form of a flat single-edge cutting blade 76 mounted at a distal end of the tubular shaft 74. The blade 76 has a width w slightly less than the diameter of the tubular shaft 74, a length l approximately equal to or greater than the length of the slots 68 in jaw inserts 62 and 64, and a thickness t suitable for sliding within slots 68. The blade shown has a straight cutting edge 78 oriented perpendicularly relative to the longitudinal axis of the instrument; however, slanted, curved, serrated or toothed cutting edges could also be used. Blade 76 extends diametrically across the open distal end of tubular shaft 74 leaving openings 80 and 82 on either side of the blade for communicating with the passage formed by the tubular shaft. Referring to FIG. 2, tubular shaft 74 is telescopically fitted within the tubular portion of intermediate member 16 and extends through aligned openings in the front and rear walls 30 and 31 of housing 12 and the front and rear endcaps 34 and 35 of hub 33 to terminate proximally outside the hub at a spherical reservoir 84 with a proximal aperture 88 and a stop cock valve 86 disposed within the reservoir for controlling passage of instruments and/or fluids through the aperture and into the tubular shaft.

A handle 90 extends transversely from tubular shaft 74 near the proximal end of the shaft and is angled proximally to form a finger rest. An insulated connector 92 enters the tubular shaft 74 on a side opposite the handle and is connected with electrically conductive elements of the instrument for performing unipolar or bipolar electric coagulation, for example using the blade 76 as a conductive element. Tubular shaft 74 also carries a transverse flange 94 disposed within hub 33 between front and rear endcaps 34 and 35 of the hub. A bias member 100, shown as a helical coil spring, is disposed around the tubular shaft 74 and held in compression between the front endcap 34 and the inner member flange 94 to bias the inner member 22 proximally within hub 33.

Inner tubular member 22 is prevented from being inadvertently moved in a distal direction by a safety mechanism 36 disposed within the hub 33. A push-button safety mechanism is shown whereby the inner tubular member 22 can be locked in a retracted position with the inner member flange 94 abutting the rear endcap 35 by depressing the button and can subsequently be released prior to being moved distally by depressing the button a second time. It will be appreciated, however, that other safety mechanisms can be used, including rotatable levers, detents, and splined collars for example. The safety mechanism shown includes a post 37 extending radially through the hub, a bias member 38 connected between the post and the hub for biasing the post radially outward, a push-button 39 mounted on top of the post externally of the hub, a latch spring 40 disposed within the hub for engaging the post in a locked position where a lower end of the post engages the inner member flange, and a trigger 41 for releasing the latch spring to allow the post to move radially outward to an unlocked position. The post 37 is oriented transversely relative to the longitudinal axis of the inner tubular member in configuration parallel to the inner tubular member flange 94 and includes an annular flange 42 disposed within the hub. Bias member 38 is shown as a helical coil spring disposed around the post and held in tension between the hub 33 and the annular flange 42 to bias the post radially outward of the hub. Latch spring 40 is formed of a resilient strip of material configured to have a flat base 43 secured to an outer wall of the hub intermediate the front and rear endcaps and a downwardly angled arm 44 extending from a proximal end of the base toward the post. Arm 44 bends back on itself to form a latching surface 45 substantially parallel to annular flange 42. A transverse extension 46 of the arm extends from a distal end of the latching surface 45 in configuration parallel to the post. Trigger 41 is disposed proximate arm extension 46 and is pivotally mounted on a pin 47 secured to the hub. The trigger is generally L-shaped with a leg 49 overlying arm extension 46 and a leg 51 extending transversely from leg 49 and at a slight downward angle looking at FIG. 2 to be disposed beneath the annular post flange 42 when the post is in the locked position shown. A torsion spring (not shown) can be connected between the trigger and the hub to bias the trigger in a counterclockwise direction looking at FIG. 2 such that the leg 49 is normally in contact with the arm extension 46.

Handles 24 and 26 are conventional and extend through slotted opening 48 in the side wall 28 of housing 12. Referring still to FIG. 2, it will be seen that each handle is pivotally mounted on a bolt, dowel or pin 102 secured to a mounting plate 103 extending outward from side wall 28 along an edge of slotted opening 48. Proximal handle 24 includes a finger loop 104 configured to accommodate one or more fingers of the user and a shank 106 connecting the finger loop with a flattened end portion 108. Flattened end portion 108 extends into housing 12 towards intermediate member flange 56 through slotted opening 48 and protrudes distally from shank 106 to pivotally mount pin 102. Distal handle 26 includes a finger loop 110 configured to accommodate one or more fingers of the user and a shank 112 connecting the finger loop with a flattened end portion 114 in sliding contact with flattened end portion 108 and extending into housing 12 towards outer member flange 50 through slotted opening 48 and protruding proximally from shank 112 to pivotally mount pin 102.

Handles 24 and 26 are coupled with intermediate and outer members 16 and 14 using brackets 116 and 118, respectively. As best seen in FIG. 11, bracket 116 is generally U-shaped and includes forward and rearward walls 120 and 122 spaced to accommodate intermediate member flange 56 therebetween and a bend portion 124 joining the forward and rearward walls. Vertical notches 126 and 128 with semicircular bottoms 127 and 129 are formed in walls 120 and 122 with the semicircular bottoms being concentrically aligned for allowing passage of the intermediate and inner members 16 and 22 through bracket 116 while clamping intermediate member flange 56 between the forward and rearward walls of the bracket. A pair of tubular bosses 130 and 132 are mounted underneath bracket 116 in axial alignment and spaced to accommodate the flattened end portion 108 of handle 24 therebetween. A pin 134 pivotally connects the flattened end portion 108 with bosses 130 and 132. Bracket 118, shown in FIG. 12, is similar to bracket 116 and includes forward and rearward walls 136 and 138 joined by a bend 140, notches 142 and 144 with semicircular bottoms 143 and 145 for accommodating outer and intermediate members 14 and 16, and bosses 146 and 148. Flattened end portion 114 of distal handle 26 fits between bosses 146 and 148 and is rotatably held therebetween by pin 150.

Referring again to FIG. 2, a pair of mating protrusions 152 and 154 are carried at opposed locations on finger loops 104 and 110 to lock handles 24 and 26 together when rotated towards one another a predetermined angular distance corresponding to a desired resultant linear separation between brackets 116 and 118. Mating protrusions 152 and 154 are shown having serrated inside surfaces, but can have any other configuration to ratchet, mate frictionally and/or latch together when engaged.

The endoscopic instrument 10 can be provided as shown in FIG. 2 with the operating unit hub 33 attached to the forceps unit housing 12, or the operating unit 13 can be provided separately so that the hub 33 can be threadedly fitted or otherwise mated to the housing 12 by the user. The latter is particularly desirable where a number of operating unit hubs carrying various types of inner members are available, allowing the user to select an appropriate hub/ inner member combination for the particular procedure to be performed.

If the operating unit 13 is provided separately, assembly of the endoscopic instrument 10 requires that inner member 22 carried by the hub 33 be inserted through the opening in the rear wall 31 of the housing 12 and advanced distally into intermediate member 16 until ring 32 of the hub meets the threaded portion of the housing sidewall 28. Hub 33 can then be threadedly attached to housing 12 by rotating the hub until the front endcap 34 of the hub abuts the housing rear wall 31. Bias member 100 urges the inner member proximally toward the retracted position where the inner member flange 94 abuts the rear hub endcap 35 causing blade 76 carried by inner member 22 to be disposed proximally of jaws 18 and 20. As mentioned previously, the inner member 22 can be locked in the retracted position and prevented from being moved distally by use of safety mechanism 36 such that blade 76 carried by the inner member cannot be inadvertently advanced toward the jaws.

Use of the endoscopic instrument 10 of the present invention is illustrated in FIGS. 13-19, wherein the instrument 10 is shown being guided through a portal sleeve 156 positioned in a wall W of an anatomical cavity. The instrument 10 is preferably passed through the portal sleeve 156 with jaws 18 and 20 at least partly closed so that the instrument can be inserted without catching on anatomical tissue or snagging structure within the portal sleeve. Since the outer tubular member 14 is normally spring-biased to a position partly closing the jaws, the user need not exert any force on the handles of the instrument during insertion.

Figure 13:
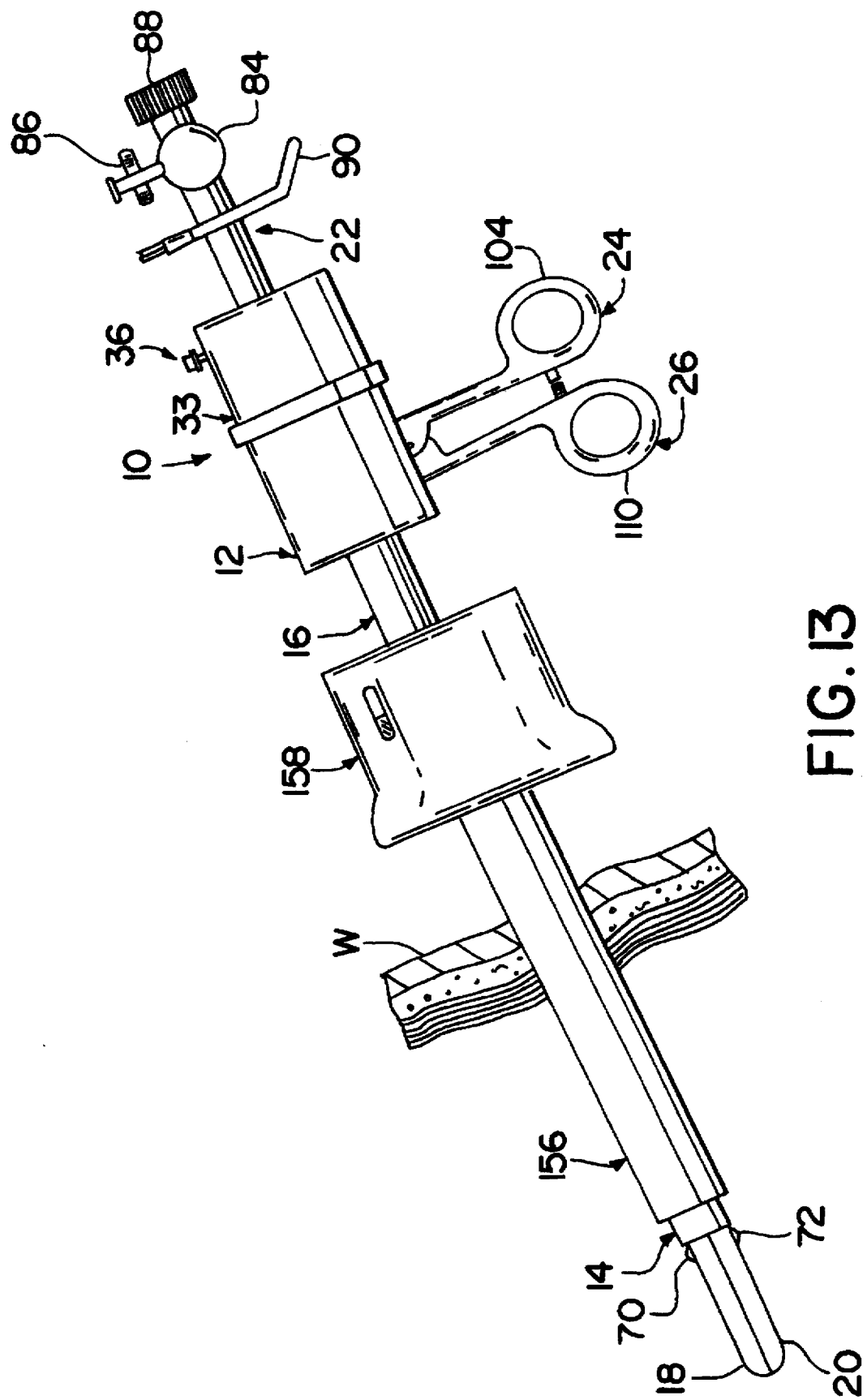
FIG. 13 is a side view, partly in section, of an endoscopic instrument according to the present invention being passed through a portal sleeve into an anatomical cavity.

With jaws 18 and 20 partly closed, the endoscopic instrument 10 is inserted through portal sleeve 156 positioned within the anatomical cavity wall W, as shown in FIG. 13, to access an operative site within the anatomical cavity. The portal sleeve 156 can be positioned in the wall using any suitable penetrating technique, including those creating puncture sites by means of removable obturators such as trocars, and is shown carrying a valve housing 158 at a proximal end to prevent the loss of pneumoperitoneum during insertion and withdrawal of the endoscopic instrument 10. Visualization of the endoscopic procedure can be accomplished using a conventional endoscope (not shown) incorporated into the endoscopic instrument 10, for example within tubular shaft 74, or separately positioned within the anatomical cavity through a second portal sleeve located at another puncture site.

Figure 14:
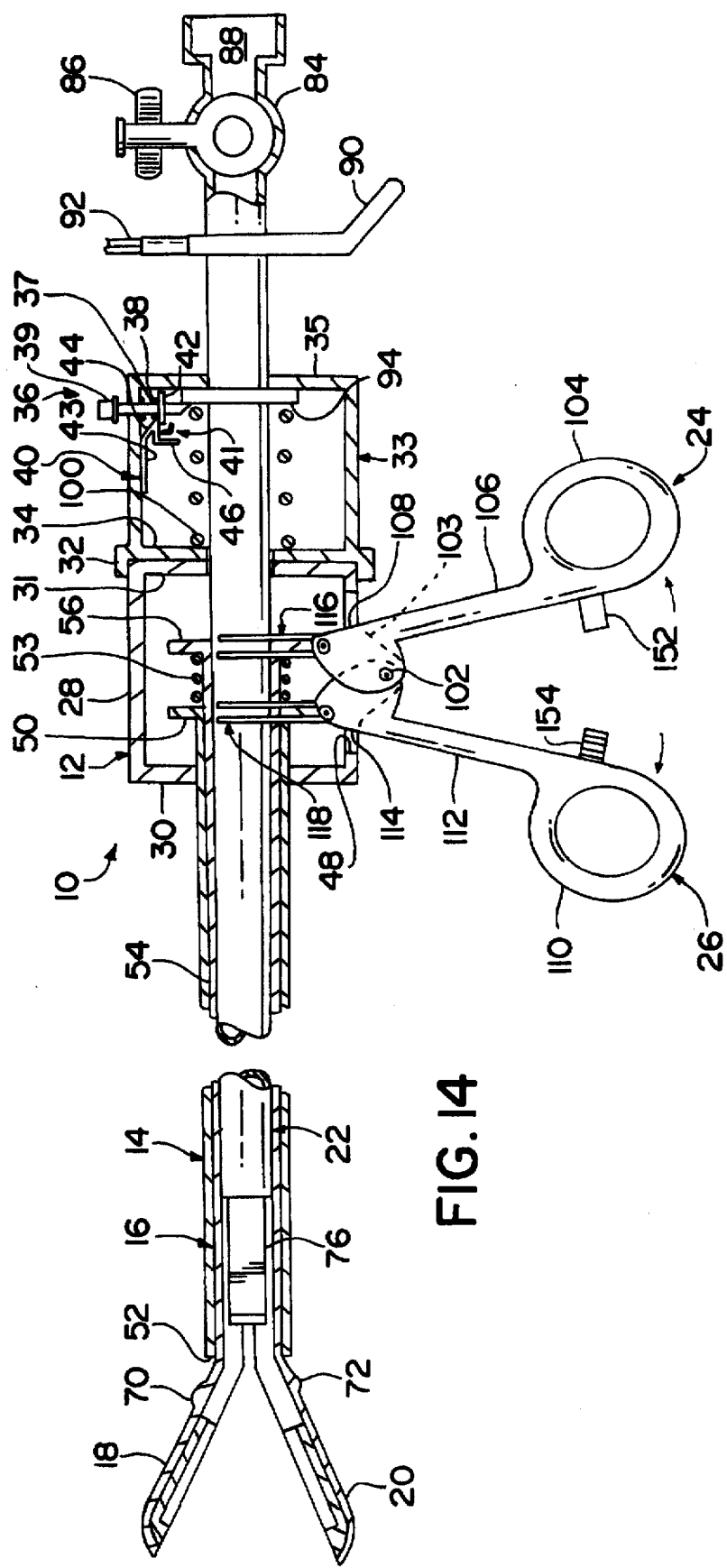
FIG. 14 is a side view, partly in section, of the endoscopic instrument of the present invention with jaws opened.

Endoscopic instrument 10 is advanced distally through portal sleeve 156 until jaws 18 and 20 emerge into the anatomical cavity. At this point jaws 18 and 20 can be opened to permit visualization through tubular shaft 74 or can remain closed in the case of a separately positioned endoscope being utilized. If the jaws 18 and 20 are to be opened, this is accomplished by exerting finger pressure on finger loops 104 and 110 against the force of bias member 53 to spread the loops apart as shown in FIG. 14. Pivotal movement of finger loops 104 and 110 about pin 102 in opposite directions causes brackets 116 and 118 to be pivoted towards one another around pin 102. The longitudinal component of the pivotal movement of brackets 116 and 118 moves outer and intermediate member flanges 50 and 56 together. Any transverse component of the bracket movement is accommodated by vertical sliding of the bracket walls against intermediate and outer member flanges 50 and 56. Movement of outer and intermediate member flanges towards one another causes the outer member distal end 52 to slide off of jaws 18 and 20 in a proximal direction allowing the jaws to spread apart elastically.

The instrument 10 can be moved within the anatomical cavity with jaws 18 and 20 in either the open or closed condition depending on the type of visualization utilized and the desirability of presenting a narrow or wide jaw profile during movement. In FIG. 15, the jaws 18 and 20 are shown in the opened condition for being positioned around anatomical tissue T to be grasped. The tissue T is located between tissue grasping inserts 62 and 64 so that when jaws 18 and 20 are partly closed, for example by releasing finger pressure on the handles 24 and 26 to allow bias member 53 to close the jaws, the tissue T will be securely held within the small gap between the jaws as shown in FIG. 16.

More specifically, when finger pressure on the handles 24 and 26 is released, bias member 53 biases flanges 50 and 56 apart, causing brackets 116 and 118 mounting the flanges to pivot in opposite directions about pin 102. Movement of the brackets 116 and 118 away from one another causes finger loops 104 and 110 to be rotated or drawn towards one another. Movement of outer and intermediate member flanges away from one another also causes the outer member distal end 52 to slide distally over jaws 18 and 20 tending to cam the jaws toward one another. At this point, jaws 18 and 20 are partly closed, i.e., separated by a small gap, and outer member distal end 52 abuts cams 70 and 72 on opposite sides of the partly closed jaws as shown previously in FIG. 2. Inner member flange 94 remains biased proximally against hub endcap 35.

Figure 17:
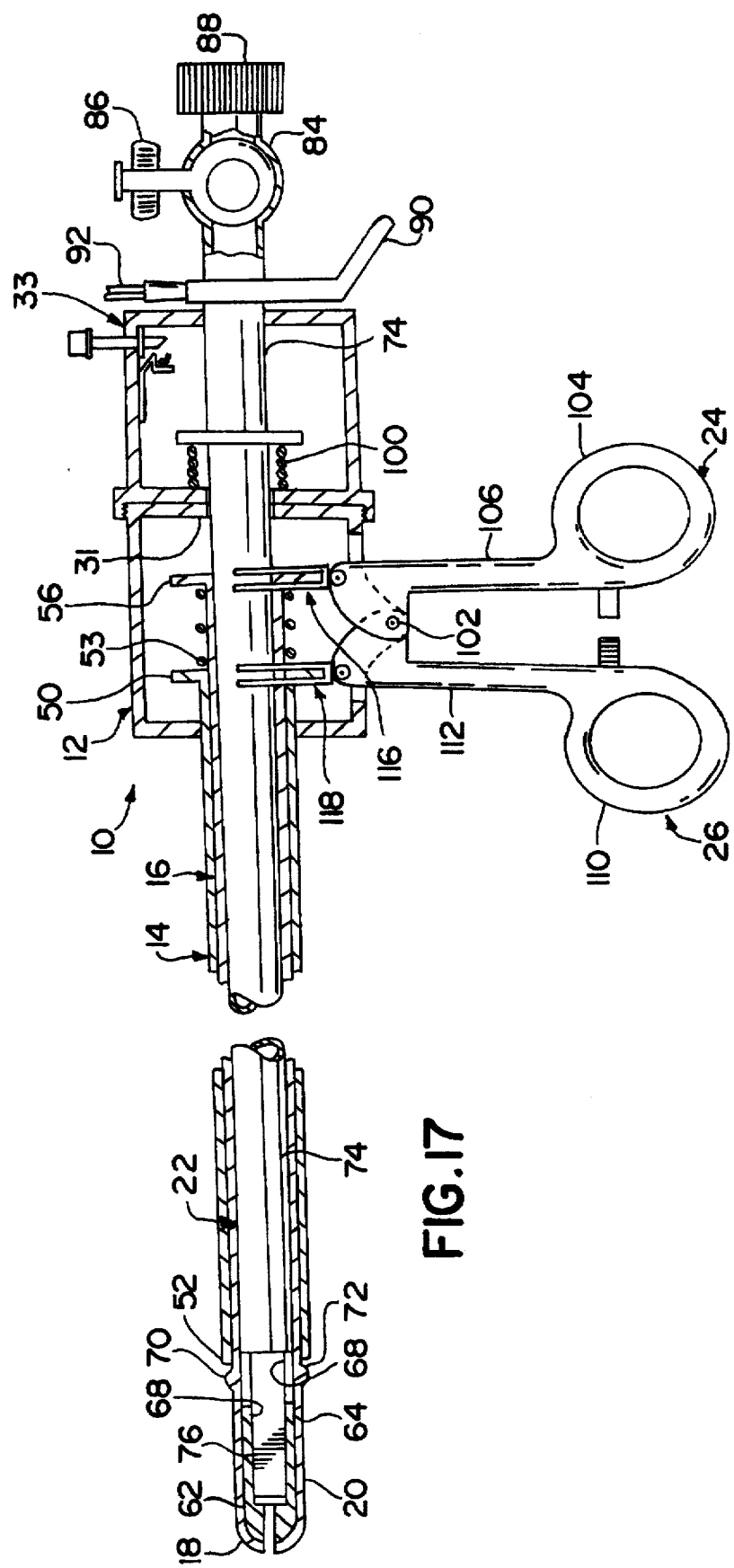
FIG. 17 is a side view, partly in section, of the endoscopic instrument of the present invention with jaws partly closed and the inner member advanced distally.

With tissue T firmly grasped between jaws 18 and 20 as illustrated in FIG. 16, inner member 22 can be advanced distally as shown in FIG. 17 to move the blade 76 along insert grooves 68 thereby cutting through the anatomical tissue T held between the jaws. First, safety mechanism 36 is released by pressing down on the push-button 39 to cause the annular flange 42 formed on the post 37 to engage the trigger leg 51 rotating the trigger clockwise looking at FIG. 2. The trigger 41 is spring-biased in a counterclockwise direction and will thus return to its original position once the annular flange 42 advances beyond trigger leg 51. When pressure on the push-button 39 is released, safety bias member 38 will draw the post 37 upward, looking at FIG. 2, so that the flange 42 will engage trigger leg 51 from the other side causing the trigger 41 to rotate counterclockwise and trigger leg 49 to bear against arm extension 46. Arm extension 46, and thus latching surface 45, are moved away from the post permitting bias member 38 to move the post to its unlocked position shown in FIG. 17 where the annular flange abuts the outer wall of the hub.

With the safety mechanism disabled, the inner member 22 can be advanced by moving handle 90 toward hub 33. Blade 76 at the distal end of the inner member is aligned with the grooves 68 formed in the jaw inserts, for example by use of splines formed along the length of the inner member, and is slidable along the grooves to cut any tissue held between the jaws. Since the grooves shown do not extend the entire length of the jaws, the distal ends of the grooves 68 can also serve as stops or abutments limiting the distal movement of the blade when the jaws are closed to protect surrounding organ structures. The tissue T can be completely or partly cut as desired and will be held between jaws 18 and 20 until the jaws are opened, allowing further procedures, such as cauterization, to be performed with the tissue immobilized. As mentioned previously, tubular shaft 74 is hollow and can thus be utilized for creating suction during the procedure, performing aspiration or irrigation or to facilitate passage of additional instruments or fluids into the anatomical cavity as desired. After a cutting procedure, blade 76 can be automatically retracted under the influence of bias member 100 or the jaws can be opened to release the tissue and the instrument manually withdrawn.

Cutting can be accomplished without grasping using the endoscopic instrument 10 in the manner illustrated in FIG. 18. Use of the instrument 10 proceeds essentially as described above for a grasping and cutting procedure; however, inner member 22 is moved distally with jaws 18 and 20 in the open condition. With the cutting edge 78 of blade 76 exposed, the instrument 10 can then be advanced against anatomical tissue or other objects and suitably manipulated to create cuts of varying length and depth. Blade 76 can be locked in the extended position shown or any other position relative to the hub by use of additional buttons, like that of safety mechanism 36, or using any other type of known locking mechanisms.

Figure 19:
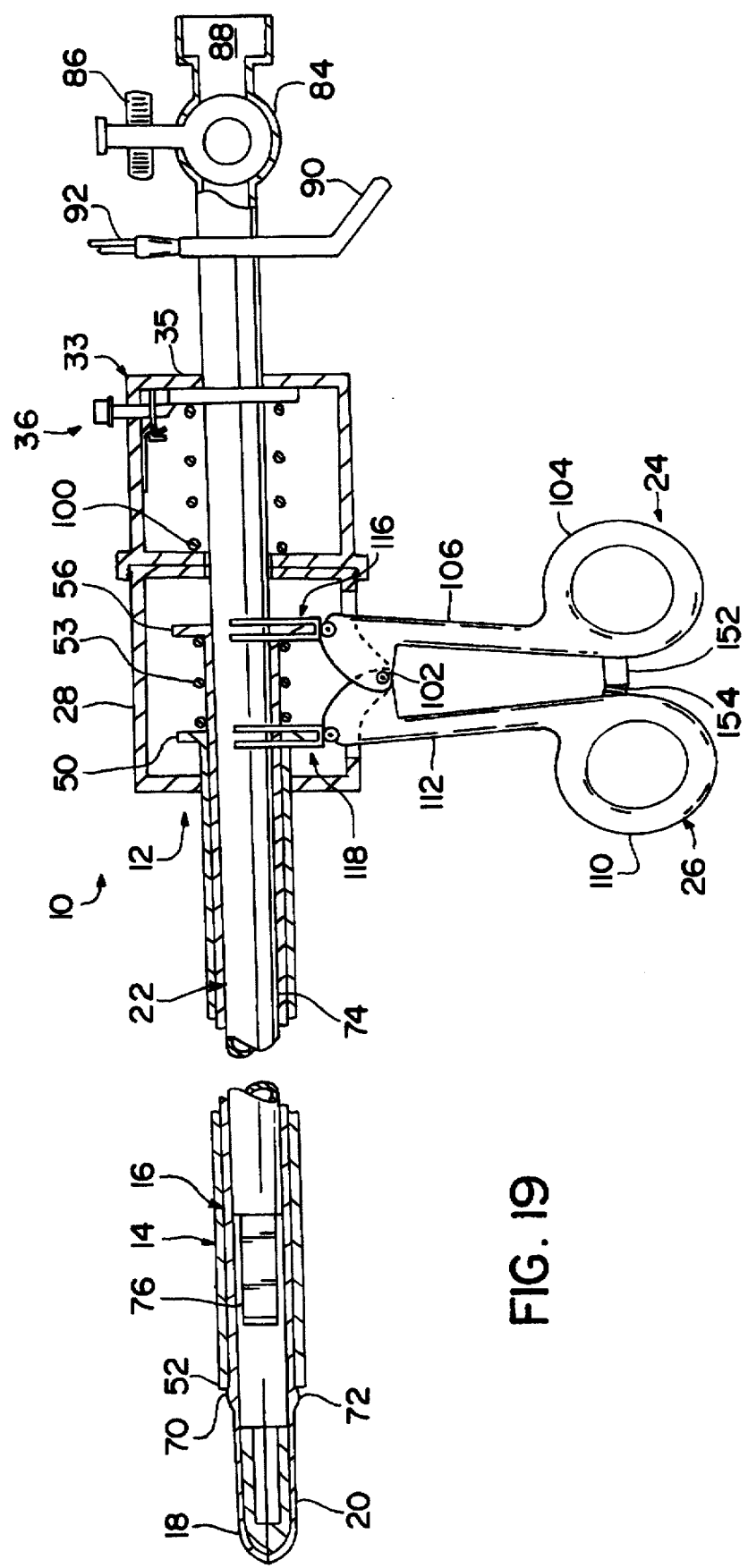
FIG. 19 is a side view, partly in section, of the endoscopic instrument of the present invention with jaws completely closed.

As mentioned previously, tissue can be grasped and securely held with jaws 18 and 20 partly closed; however, for certain procedures it may be desirable to draw the jaws completely together as shown in FIG. 19, with or without objects held between the jaws. The jaws 18 and 20 can be closed completely or clamped together by drawing finger loops 104 and 110 towards one another until outer member distal end 52 slides distally over cams 70 and 72 to force the jaws into close contact with one another. If tissue or some other object is disposed between the jaws, advancement of the outer member 14 over the cams 70 and 72 will result in greater compression of the object. When loop handles 104 and 110 are drawn sufficiently close to one another, mating protrusions 152 and 154 will be engaged, locking the handles in their current position. If the mating protrusions 152 and 154 are ratcheted as shown, various degrees of compression can be achieved and maintained without continuous finger pressure being applied. Closure of forceps jaws 18 and 20 also helps prevent passage of fluids through intermediate and inner members 16 and 22 of the endoscopic instrument, allowing the operating unit (including hub 33 and inner member 22) to be replaced with minimum loss of pneumoperitoneum.

Replacement of operating unit 13 involves unscrewing the hub 33 from housing 12 and withdrawing the hub along with inner member 22 to permit a new operating unit hub carrying a different type of inner member to be inserted for performing other functions, such as, for example, cutting, grasping, hooking, manipulating, dissecting, collecting tissue for biopsy, penetrating, injecting, creating suction, aspirating, irrigating, cauterizing, suturing, ligating, visualizing and illuminating. During substitution of operating units, the opening in the rear wall of the housing can be closed using a finger or conventional valves, such as flapper or trumpet valves, to help prevent loss of pneumoperitoneum.

Figure 20:
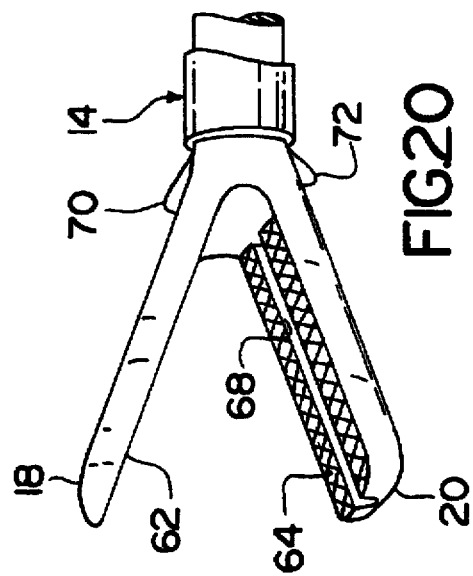
FIG. 20 is a fragmentary perspective view of an alternative jaw configuration for the endoscopic instrument according to the present invention.
Figure 21:
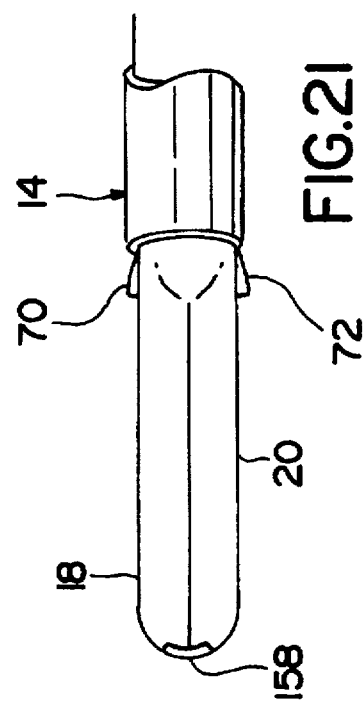
FIG. 21 is a side view of the jaws of FIG. 20 in a closed condition.

A modification of the endoscopic instrument 10 of the present invention is illustrated in FIGS. 20 and 21 wherein jaws 18 and 20 and tissue grasping jaw inserts 62 and 64 are formed as an integral one-piece construction and grooves 68 are made to extend along the length of the tissue grasping inserts 62 and 64 to define an aperture 158 at the distal end of jaws 18 and 20 when the jaws are closed. Aperture 158 can be used for extending blade 76 and other operating members distally beyond jaws 18 and 20 or for permitting passage of needles and other operating members through jaws 18 and 20 when the jaws are closed.

Figure 22:
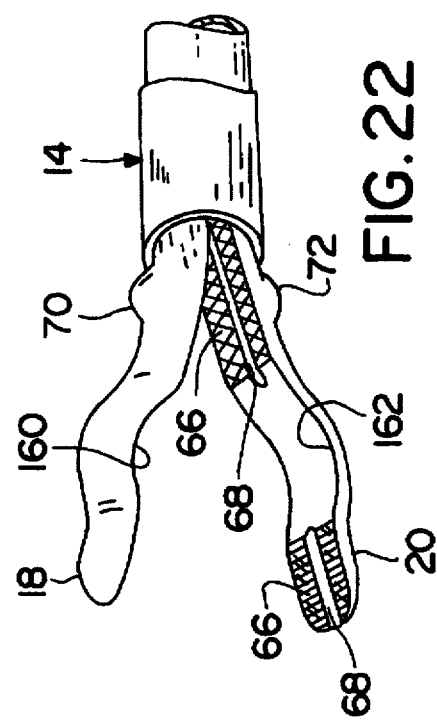
FIG. 22 is a fragmentary perspective view of another jaw configuration for the endoscopic instrument of the present invention.

FIG. 22 shows a further modification of the endoscopic instrument 10 of the present invention in which jaws 18 and 20 include arcuate or concave portions 160 and 162, respectively, integrally-formed at opposed locations along the length of the jaws. Arcuate portions 160 and 162 cooperate to define a substantially circular transverse passage through jaws 18 and 20 when the jaws are closed and can thus hold a tubular organ, other anatomical tissue or an object therebetween for being manipulated or cut without compressing or flattening the organ, tissue or object. Tissue gripping surfaces 66 are shown formed on the flat portions of jaws 18 and 20 but can be formed along the arcuate portions as well. Grooves 68 are interrupted by the arcuate portions 160 and 162 but extend longitudinally along the flat portions of the jaws and are aligned to form a track for guiding blade 76 or other operating members across the arcuate portions; and, when the grooves extend the entire length of the jaws as shown, the grooves can define an aperture such as aperture 158 at the distal end of the jaws.

Figure 23:
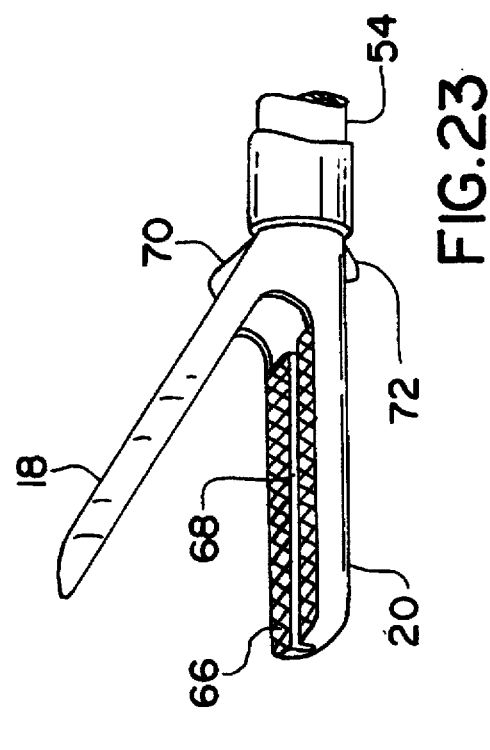
FIG. 23 is a fragmentary perspective view of yet another jaw configuration for the endoscopic instrument of the present invention.

In yet another modification of the endoscopic instrument 10 of the present invention, shown in FIG. 23, the lower jaw 20 is fixed and extends distally from tubular body 54 along a longitudinal axis of the tubular body. Upper jaw 18 in FIG. 23 carries a cam 70 and is movable from an open position normally extending at an angle relative to the longitudinal axis of tubular body 54 to a closed position where it mates with fixed lower jaw 20. Fixed lower jaw 20 can also carry a cam 72. Jaws 18 and 20 include tissue gripping surfaces 66 and grooves 68 formed along the length of the tissue gripping surfaces to serve as a guide for blades and other operating members and to form a distal aperture such as aperture 158.

Another modification of jaws 18 and 20 is shown in FIGS. 24 and 25 wherein the jaws carry a pair of cutting blades 164 and 166 in opposed relation near a central longitudinal axis of the jaws. Blades 164 and 166 depend perpendicularly from tissue gripping surfaces 66 of the jaws and have opposed cutting edges 168 and 170 spaced apart when jaws 18 and 20 are open to permit positioning of anatomical tissue between the blades. When jaws 18 and 20 are closed, blades 164 and 166 move towards one another and into scissor-like sliding contact to cut any tissue held between the jaws. As best seen in FIG. 25, the presence of blades 164 and 166 between jaws 18 and 20 prevents complete closure of the jaws and thus can be useful where compression or flattening of the tissue is not desired or important. Slight separation of jaws 18 and 20 also facilitates visualization of the procedure through the endoscopic instrument. If it is desired that jaws 18 and 20 move closer to one another, elongate pockets, shown in phantom at 165, can be formed in the tissue gripping surfaces 66 alongside the blades 164 and 166 to receive opposed cutting edges 168 and 170.

FIGS. 26 and 27 illustrate a further modification wherein upper jaw 18 carries a centrally located blade 164 with cutting edge 168 and lower jaw 20 defines a concave pocket 172 for receiving blade 164. Cutting edge 168 is angularly spaced from the lower jaw 20 when the jaws are open permitting anatomical tissue to be positioned between the blade 164 and pocket 172. When jaws 18 and 20 are closed, blade 164 moves toward pocket 172 and is received therein to cut any tissue held between the jaws. As seen in FIG. 27, jaws 18 and 20 can be closed completely when blade 164 is disposed within pocket 172 and can thus compress or flatten any tissue held therebetween if desired.

The jaws 18 and 20 shown in FIGS. 28 and 29 carry a pair of blades 164 and 166 in opposed relation along lateral edges of the jaws. Blades 164 and 166 depend perpendicularly from opposed lateral edges of the jaws and have opposed cutting edges 168 and 170 spaced apart when jaws 18 and 20 are open to permit positioning of anatomical tissue between the blades. When jaws 18 and 20 are closed, blades 164 and 166 move towards one another and into sliding contact to cut any tissue held between the jaws. As best seen in FIG. 29, the presence of blades 164 and 166 between jaws 18 and 20 prevents complete closure of the jaws and thus can be useful where compression or flattening of the tissue is not desired or important. The slight separation of jaws 18 and 20 and the off-axis or eccentric position of the blades also facilitates visualization of the procedure through the endoscopic instrument. Additionally, one or both of the upper and lower jaws 18 and 20 can have a groove 68 formed longitudinally along a tissue gripping surface 66 so that other instruments can be advanced centrally through the jaws 18 and 20 when closed for performing various functions. If it is desired that jaws 18 and 20 move closer to one another, elongate pockets (not shown) can be formed in the tissue gripping surfaces 66 alongside the blades 164 and 166 to receive opposed cutting edges 168 and 170.

FIGS. 30 and 31 illustrate a further modification wherein upper jaw 18 carries an off-axis blade 164 with cutting edge 168 and lower jaw 20 defines a concave pocket 172 for receiving blade 164. Cutting edge 168 is angularly spaced from the lower jaw 20 when the jaws are open permitting anatomical tissue to be positioned between the blade 164 and pocket 172. When jaws 18 and 20 are closed, blade 164 moves toward pocket 172 and is received therein to cut any tissue held between the jaws. As seen in FIG. 31, jaws 18 and 20 can be closed completely when blade 164 is disposed within pocket 172 and can thus compress or flatten any tissue held therebetween if desired.

Blades 164 and 166 in any of the jaw configurations described above can also have distal cutting edges (like cutting edge 78 for blade 76) for being advanced against anatomical tissue by distal movement of jaws 18 and 20.

Further, the opposed cutting edges 168 and 170 can be slightly offset from one another as shown to provide a scissor-like cutting action or can be directly aligned to abut when closed thereby providing a chopping action if desired.

As mentioned previously, hub 33 can be removed from housing 12 by unscrewing the ring 32 from the threaded portion of the housing 12 and withdrawing the hub along with the inner member 22. Other operating units having hubs carrying various types of inner members, such as the inner members described below, can then be threaded onto the housing for performing various functions without removing the forceps unit from the anatomical cavity. This is particularly useful where tissue is already held between jaws of the forceps unit and an inner member carrying a different type of operating member is needed for performing some operative step with the tissue held in place.

FIG. 32 shows an alternative distal configuration for an inner member 22 wherein the tubular shaft 74 terminates distally at an open end 173 carrying an operating member in the form of a coaxial needle-like protrusion 176 with a distal tissue-penetrating tip 178 and a proximal flat plate-like base 175 arranged diametrically across the open distal end 173 of the tubular shaft 94. Inner member 22 fits telescopically within intermediate member 16 and can be advanced distally in the manner described above so that needle 176 passes through jaw grooves 68 to pierce tissue held between jaws 18 and 20 or to protrude distally from aperture 158 when the jaws are closed as shown in FIG. 33. Fluids can be introduced or drawn through tubular shaft 74 via open distal end 173; and in the case of fluid introduction, the presence of the flat base 175 across the opening will tend to separate any fluid flow for increased dispersion.

The inner member 22 shown in FIG. 34 is similar to that shown in FIGS. 32 and 33 with the exception of the tubular shaft 74 terminating distally in an inwardly tapered frusto-conical portion 174 carrying a coaxial needle-like protrusion 176 with a sharp tissue-penetrating tip 178. The needle-like protrusion 176 is hollow and has a beveled opening 180 at a distal end for allowing passage of fluids through the needle. The peripheral edge of beveled opening 180 defines the sharp tissue-penetrating tip 178 of the needle and can be used for penetrating anatomical tissue held between jaws 18 and 20 or can be protruded distally from aperture 158 when the jaws are closed. Various fluids can be precisely administered or extracted from the anatomical tissue or cavity using hollow needle 176 with valve 86 opened and proximal aperture 88 connected with appropriate instrumentation such as suction lines, fluid sources or any other fluid handling apparatus.

The inner member distal configurations shown in FIGS. 35 and 36 are similar to those illustrated in FIGS. 32 and 33, but with needle-like protrusions 176 being offset from the central longitudinal axis of each tubular shaft 74. The needle-like protrusion 176 of the inner member 22 shown in FIG. 35 is movable along a groove 68, such as that shown in the fixed lower jaw 20 of FIG. 23, but is hollow and has a beveled distal opening 180 for allowing passage of fluids through the needle as described above. The needle-like protrusion 176 of inner member 22 shown in FIG. 36 is solid and is also movable along groove 68 in the fixed lower jaw 20 shown in FIG. 23 for protruding distally from aperture 158 when jaws 18 and 20 are closed.

FIG. 37 shows another alternative distal configuration for inner member 22 wherein tubular shaft 74 terminates distally in a pair of pivoted scissor blades 182 and 184. Scissor blades 182 and 184 are configured to fit within grooves 68 in movable jaws 18 and 20 as shown in FIG. 38 and include opposed cutting edges 186 and 188. Proximal ends of blades 182 and 184 are pivotally mounted on a pin 190 secured to a flat base 191 extending distally from tubular shaft 74. Blades 182 and 184 are biased apart with a bias member such as a torsion spring (not shown) disposed around pin 190 and connected between the blades. Inner member 22 can be biased distally within hub 33 or can be fixed to the hub. If biased, the inner member can be advanced into intermediate member 16 by threadedly engaging hub 33 to housing 12, for example, and is positioned between jaws 18 and 20 by distal movement of handle 90. If fixed, the inner member is advanced between jaws 18 and 20 simply by mounting the hub 33 to housing 12. Blades 182 and 184 are movable to be pivoted together for passage through intermediate member 16 and will spring away from one another into grooves 68 upon advancing distally between jaws 18 and 20 of the endoscopic instrument 10. With the blades 182 and 184 seated within grooves 68, cutting is accomplished by opening the jaws 18 and 20 in the manner previously described (i.e., by separating loop handles 104 and 110), positioning the anatomical tissue between the blades, and releasing the loop handles to permit the jaws to close around the tissue. Cutting edges 186 and 188 of blades 182 and 184 slidingly contact one another to cut anatomical tissue held therebetween or can be directly aligned to perform a chopping-type cut. If tubular shaft 74 is open at a distal end, fluids can be introduced or drawn out of the anatomical cavity via the distal opening prior to, during or after a cut is made. The inner member 22 can then be withdrawn proximally from jaws 18 and 20 by releasing handle 90 if inner member 22 is biased, or by uncoupling hub 33 from housing 12. In either case, blades 182 and 184 are cammed together about pivot 190 within intermediate member 16 during passage of the inner member through the intermediate member.

The inner member 22 shown in FIG. 39 includes a pair of scissor blades 182 and 184 like those described above but with the lower scissor blade 184 being fixed to extend longitudinally and the upper scissor blade 182 being pivotally mounted on a pin 190 secured to a flat base 191 extending distally from the tubular shaft 74. The upper blade 182 is biased away from the fixed lower blade 184 with a bias member (not shown) and, when fitted within jaws 18 and 20 such as those shown in FIG. 40, is movable toward the lower blade by closing the jaws.

FIG. 41 illustrates another modification of the inner member 22 of endoscopic instrument 10 wherein the distal end of tubular shaft 74 is cut along a longitudinal axis to form a pair of opposed biopsy box members 192 and 194. Biopsy box members 192 and 194 are preferably formed integrally with tubular shaft 74 as a unitary piece and are resiliently biased apart to fit within grooves 68 of any of the pivoted jaws described herein, such as those shown in FIG. 42. The box members 192 and 194 can have any configuration in cross-section, for example semi-cylindrical or rectangular, for defining opposed cavities 196 and 198 and cooperating to form a tissue-receiving container when closed as shown in FIG. 43. Respective peripheral edges of the biopsy box cavities are configured to form opposed cutting surfaces 200 and 202 for cutting samples from anatomical tissue held between jaws 18 and 20 when the jaws are closed. The cutting surfaces 200 and 202 can be arranged relative to one another as shown for sliding contact to perform a scissor-like cut or for direct abutment to perform a chopping cut. When a tissue sample T is collected within biopsy box members 192 and 194, inner member 22 can be removed from intermediate member 16, for example by uncoupling hub 33 from housing 12, and another inner member inserted or the entire instrument 10 removed for retrieval of the biopsy specimen.

The inner member 22 shown in FIG. 44 is similar to that shown in FIG. 41 but with the lower biopsy box 194 fixed to extend longitudinally from tubular shaft 74 and the upper biopsy box 192 being resiliently movable. The upper biopsy box 192 is biased away from the fixed lower biopsy box 194 and, when fitted within a jaw 18 such as that shown in FIG. 45, is movable toward the fixed biopsy box 194 by closing of the movable jaw 18 against the fixed jaw 20.

FIGS. 46 and 47 illustrate yet another modification of the inner member 22 of the endoscopic instrument 10 wherein the distal end of the tubular shaft 74 is closed by a forward wall 204 and carries a distally extending hook 206. Hook 206 terminates proximally at a base plate 208 extending perpendicularly from wall 204 and includes a solid shank 210 extending distally from a lower or transverse edge of the base plate 208 to terminate at a substantially U-shaped needle 212 having a blunt or sharp tip extending proximally toward base plate 208. Shank 210 of hook 206 can be fitted within a groove 68 extending through a lower jaw, such as the fixed lower jaw 20 shown in FIG. 48, so that the curved needle 212 protrudes distally beyond the jaw. Axial movement of tubular shaft 74 within intermediate member 16 advances and retracts the hook 206 relative to jaws 18 and 20 so that when the jaws are closed, hook 206 can be used in cooperation with the upper and lower jaws 18 and 20 to capture anatomical tissue T in the region between the curved needle 212 and the distal end of the jaws as shown in FIG. 49. Hook 206 can also be configured for use as a cautery or to snag, puncture or manipulate anatomical tissue as desired.

Figure 50:
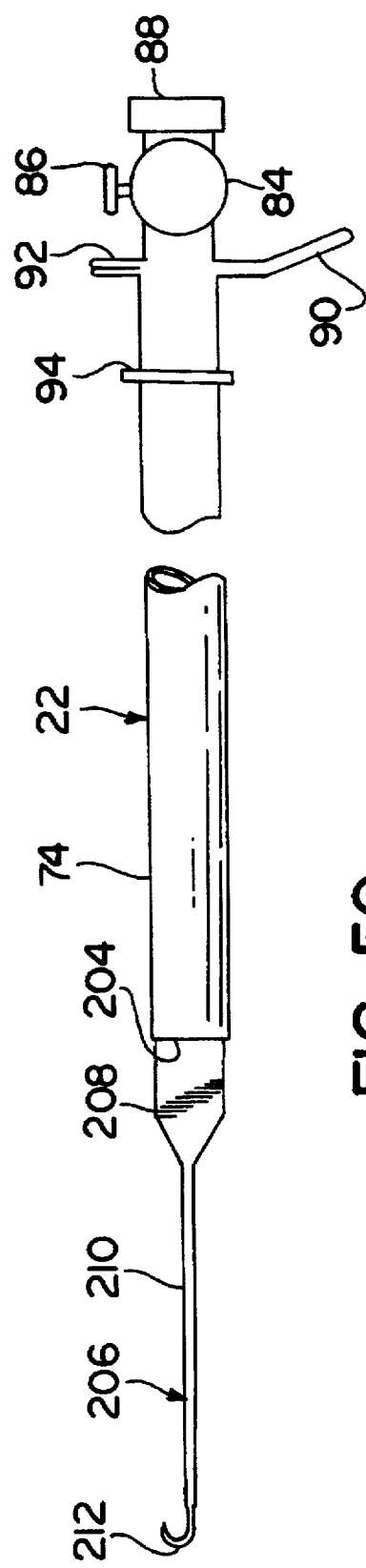
FIG. 50 is a side view, broken longitudinally, of an alternative inner member carrying a hook for use with the endoscopic instrument of the present invention.
Figure 51:
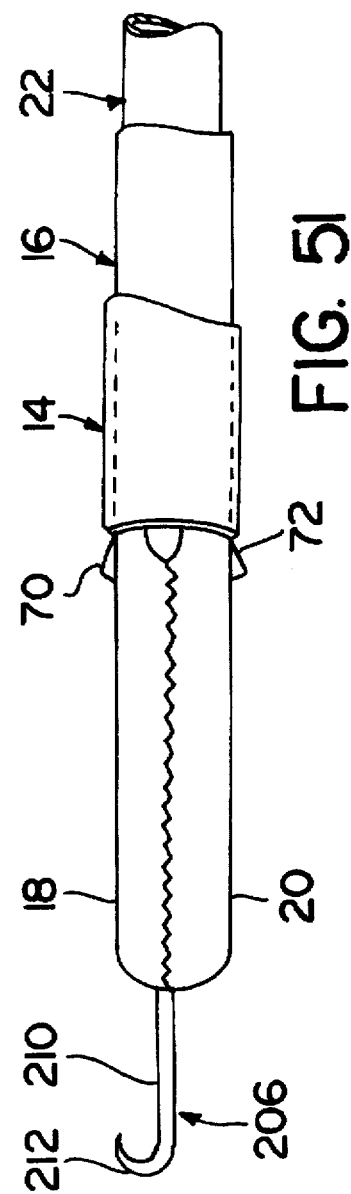
FIG. 51 is a fragmentary side view of the hook of FIG. 50 protruding distally from closed forceps jaws.

Another inner member 22 carrying a solid hook is illustrated in FIG. 50 and is similar to the inner member shown in FIG. 46 with the exception of the shank 210 extending from base plate 208 along a central longitudinal axis of tubular shaft 74 and the curved needle 212 having a smaller radius of curvature to facilitate passage of the needle through intermediate member 16. Shank 210 fits within slots 68 of upper and lower forceps jaws 18 and 20 as shown in FIG. 51 and can be used as a cautery or to snag, capture, puncture or manipulate anatomical tissue depending on the procedure being performed. The tubular shafts 74 of the inner members shown in FIGS. 46 and 50 can also have open distal ends for permitting passage of fluids therethrough and, in the case of open distal ends, each base 208 will then be disposed diametrically across the open distal end.

The inner members shown in FIGS. 52 and 53 are similar to those shown in FIGS. 46 and 50, respectively, but without base plates 208 and with shanks 210 and curved needle portions 212 being hollow. Tubular shaft 74 for each of the inner members 22 terminates distally in a front wall 204 and each hollow shank 210 extends distally from an opening in the front wall 204 to terminate at a hollow curved needle 212 with an aperture 214 at a tip for passage of fluids, such as vasoconstricting medicaments, or lengths of suture material therethrough.

FIG. 54 illustrates another inner member 22 similar to that shown in FIG. 52 but with a continuous channel 216 formed along an inside surface of the shank 210 and needle 212. Fluid passing through a small opening in distal wall 204 proximate channel 216 is directed along channel 216 to form a diffuse flow in the region about the channel. The inner member 22 shown in FIG. 55 is similar to that shown in FIG. 54 with the exception of tubular shaft 74 having an open distal end 218 for creating an even more diffuse flow or permitting passage of other implements therethrough.

The needle 212 for the inner member 22 shown in FIG. 56 is straight and extends perpendicularly from shank 210. A channel 216 is formed along an inside surface of the shank 210 and needle 212 from a small opening in wall 204 at the distal end of tubular shaft 74 to the tip of the needle.

Another modified inner member is illustrated in FIGS. 57 and 58, wherein the modified inner member 22 includes a tubular shaft 74 having an open distal end 218 carrying a perpendicularly angled hook 206. Hook 206 terminates proximally at a base plate 208 extending diametrically across open distal end 218 of tubular shaft 74 and includes a solid shank 210 extending distally from a lower edge of the plate to terminate at a perpendicular needle 212. The inner member 22 shown in FIG. 59 is similar to that shown in FIG. 57 but with a curved, rather than straight, needle 212. Needles 212 for the inner members shown in FIGS. 57 and 59 are shown having relatively blunt tips 213 for contacting anatomical tissue without penetrating into the tissue. It will be appreciated, however, that tips 213 can be sharp to penetrate anatomical tissue if desired.

When an inner member 22 such as that shown in FIG. 55 has an open distal end 218, tubular implements can be introduced into the tubular shaft 74 through aperture 88 and advanced distally to emerge through the open distal end 218 of the tubular shaft. FIG. 60 illustrates an exemplary tubular instrument 220 insertable through tubular shaft 74 and having a tubular body 222 carrying a cutting blade 224 at a distal end. Cutting blade 224 includes a distal cutting edge 226 configured to fit within the channel 216 formed in needle 212 as shown in FIG. 61. In use, inner member 22 can be positioned with needle 212 extending distally from closed jaws 18 and 20 to capture tissue between the needle and the distal end of the jaws and tubular implement 220 can be advanced distally through tubular shaft 74 until blade 224 slides along channel 216 and through an aperture (such as aperture 158 in FIG. 21) to cut the tissue held between the needle and the jaws.

Figure 62:
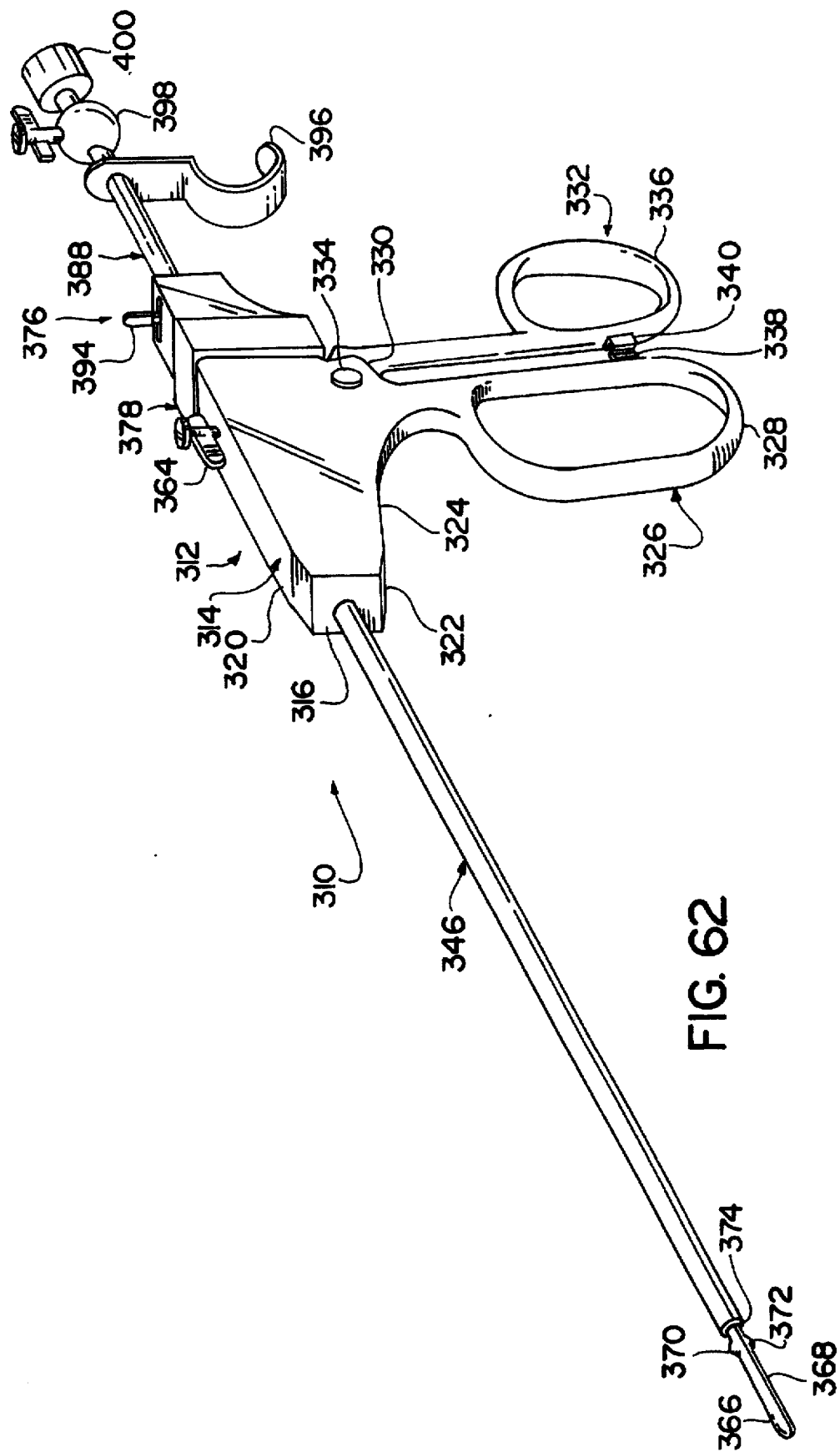
FIG. 62 is a perspective view of another modified endoscopic instrument according to the present invention.
Figure 63:
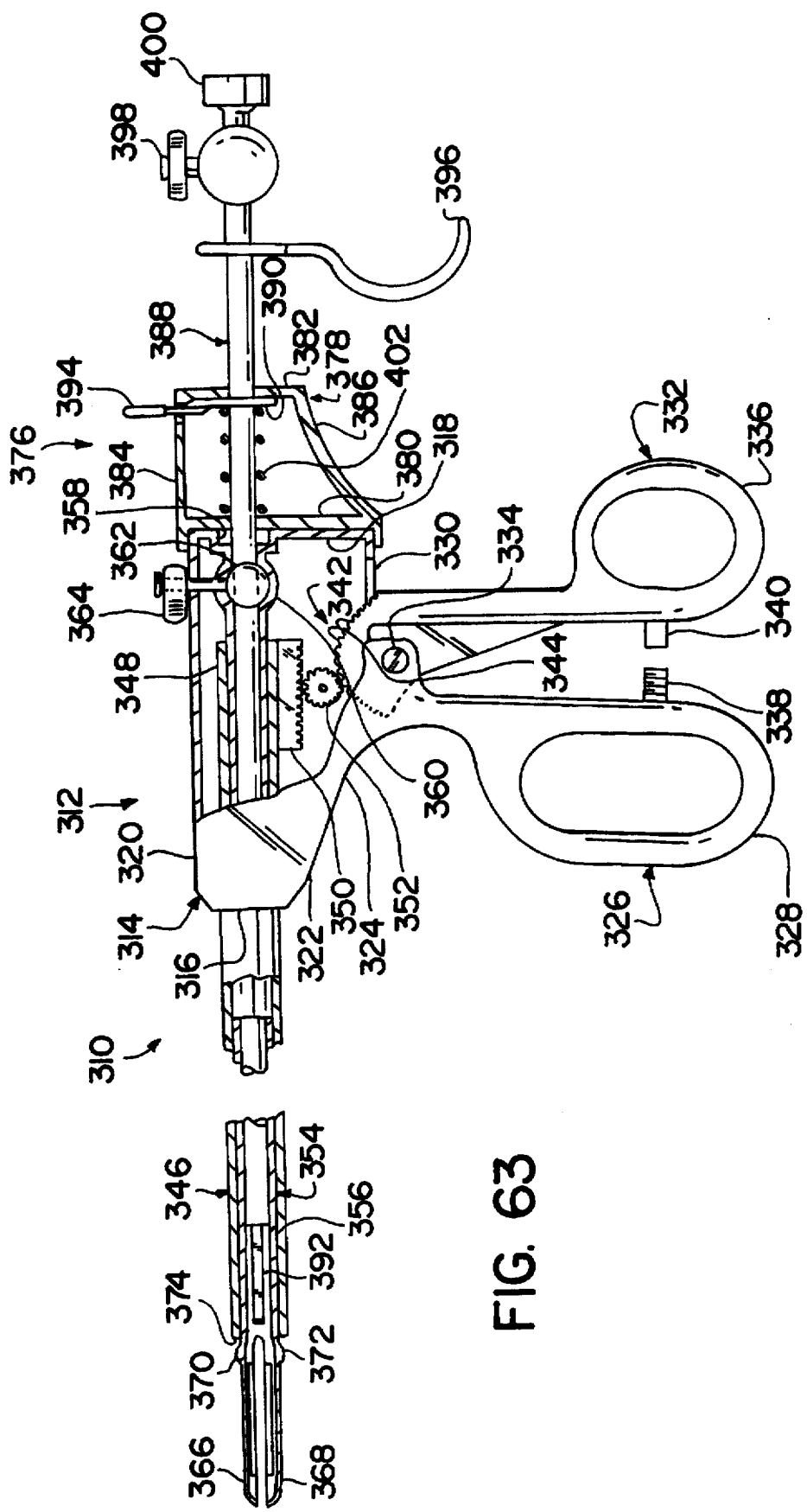
FIG. 63 is a side view, partly in section, of the modified endoscopic instrument of FIG. 62.

A modification of the endoscopic instrument of the present invention is shown in FIGS. 62 and 63 at 310. The modified endoscopic instrument 310 is similar to endoscopic instrument 10 with the exception of one handle being fixed to the forceps unit and the other handle being movable to drive a rack and pinion drive mechanism for advancing the outer tubular member distally over the forceps jaws. Forceps unit 312 for the endoscopic instrument 310 includes a generally rectangular housing 314 having longitudinally spaced front and rear walls 316 and 318 oriented perpendicular to a longitudinal axis of the instrument, a top wall 320 in configuration parallel to the longitudinal axis, and a bottom wall 322 having a concave portion 324 curving downward from the front wall to form a handle 326 with an elongate finger loop 328 configured to accommodate one or more fingers of a user and a straight portion 330 extending proximally from an upper end of the handle in configuration parallel to the top wall. A movable handle 332 is pivotally mounted on a pin 334 proximally spaced from the fixed handle 326 and secured to a wall or walls of the housing. A lower end of the handle 332 is configured as a finger loop 336 to accommodate one or more fingers of the user and a pair of mating protrusions 338 and 340 are carried in opposed relation on finger loops 328 and 336 for ratchet-like engagement during operational use. As best seen in FIG. 63, handle 332 includes an arcuate end portion 342 disposed within the housing 314 and defining a plurality of gear teeth 344 on a side of the pin 334 opposite finger loop 336.

An outer tubular member 346, similar to outer tubular member 14 for endoscopic instrument 10, extends distally from housing 314 through an opening in the front wall 316 of the housing. A proximal end 348 of the outer tubular member 346 is movably disposed within the housing and carries a rack 350 in spaced relation to the toothed end portion 342 of handle 332. A pinion gear 352 is meshed between the rack 350 and toothed end portion 342 of the handle to convert rotary or pivotal movement of the handle into linear movement of the rack. Looking at FIG. 63, it will be appreciated that counterclockwise rotation of handle 332 about pin 334 results in proximal movement of the outer tubular member 346 relative to the housing and that clockwise rotation of the handle 332 about pin 334 results in distal movement of the outer tubular member relative to the housing. In a preferred embodiment, movable handle 332 is biased in a clockwise direction toward fixed handle 326, for example by use of a torsion spring (not shown) coiled around pin 334 and connected between the movable handle and the fixed handle and/or the housing.

An intermediate member 354 includes a tubular portion 356 having a proximal end fixed to the rear wall 318 of the housing and configured to form a recess 358 in the rear wall for coupling medical instruments and accessories with the forceps unit and a spherical reservoir 360 distally spaced from the recess. A spherical valve member 362 is disposed within the reservoir and connected with a knob 364 externally of the housing for operation of the valve. The tubular portion 356 of the intermediate member terminates distally at a pair of integrally formed jaws 366 and 368, similar to jaws 18 and 20, protruding distally from the outer tubular member 346. With outer tubular member 346 in the rest position shown in FIG. 63, jaws 366 and 368 are partly closed together and cams 370 and 372 are distally spaced from the distal end 374 of the outer tubular member.

Operating unit 376 for endoscopic instrument 310 is essentially the same as operating unit 13 for endoscopic instrument 10 but is suitably shaped to fit telescopically over the rear portion of housing 314. Hub 378 for operating unit 376 is generally rectangular with front and rear end walls 380 and 382, a top wall 384 and an inwardly curved or concave bottom wall 386. Top and bottom walls of the hub are joined by lateral sidewalls and extend distally beyond the front end wall to form a rectangular recess configured to receive and frictionally engage the forceps unit housing. Inner member 388 is the same as inner member 22 and includes a proximally-biased flange 390 disposed between front and rear end walls of the hub. The distal end of the inner member 388 is shown carrying a blade 392 but can carry any kind of operating member described herein. A lever 394 extends through the top wall of the hub and is pivotally mounted on a pin 396 secured to the hub near the rear end wall for rotation about a central portion of the lever. A lower end of the lever 394 extends a suitable distance into the hub for engaging the inner member flange 390 in a retracted position to lock the inner member from distal movement. Handle 396, stopcock valve 398 and coupling 400 are the essentially the same as handle 90, valve 86 and coupling 88 for endoscopic instrument 10.

Operation of the modified endoscopic instrument 310 is essentially the same as for endoscopic instrument 10 with the exception that intermediate member 354 is held stationary relative to the housing 314 while outer tubular member 346 is permitted to move. As a result, jaws 366 and 368 can be drawn together or separated without the need of being moved axially and can therefore be precisely positioned and maintained at a desired axial position while being opened or closed. Movement of the outer tubular member over the intermediate member is controlled by operation of movable handle 332. Counterclockwise rotation of handle 332 about pin 334 results in clockwise rotation of pinion 352 which engages rack 350 to cause proximal movement of the outer tubular member 346 relative to jaws 366 and 368 thereby permitting the jaws to open. Conversely, clockwise rotation of the handle 332 about pin 334 results in counterclockwise rotation of pinion 352 which engages rack 350 to cause distal movement of the outer tubular member relative to the jaws causing the jaws to close.

Movable handle 332 is preferably proximally spaced from fixed handle 326 as shown so that the user can maintain one or more fingers on the stationary handle 326 while operating the movable handle 332 or the inner member handle 396 with the thumb and/or other fingers of the hand. Movable handle 332 is preferably biased toward stationary handle 326 so that when the movable handle is released, for example to operate the inner member handle 396, outer tubular member 346 will be moved over jaws 366 and 368 to close the jaws together. Inner member 388 can then be moved distally against the proximal bias of spring 402 disposed within the hub by exerting a distal force on the inner member handle 396. If engaged, safety lever 394 must first be disengaged by rotating the lever until a lower end of the lever is radially spaced from the flange to allow unobstructed passage of the flange past the lever. The inner member 388 can be advanced distally until handle 396 abuts the bottom and rear walls of the hub. The curved configuration of the hub bottom wall 386 provides clearance for the arcuate portion of handle 396 allowing the arcuate portion of the handle to be spaced closer to movable handle 332 and to conform to the shape of the hub when depressed.

From the above, it will be appreciated that the endoscopic instrument of the present invention permits multiple functions to be performed endoscopically by use of a forceps unit having a tubular member with jaws configured for grasping or holding objects such as anatomical tissue or needles and a removable operating unit having an inner member telescopically fitted within the forceps unit tubular member and carrying various operating members. By "operating member" is meant any medical device, implement or accessory for performing at least one of the functions of cutting, collecting tissue for a biopsy, penetrating, injecting fluids, creating suction, aspirating, irrigating, grasping, manipulating, hooking, dissecting and cauterizing, for example. The tubular member and jaws of the forceps unit are preferably formed as an integral one-piece construction and are movably disposed within an outer tubular member to permit sliding movement of the outer tubular member over the jaws. The outer member and tubular forceps member can be mounted by a housing and coupled using any suitable handle mechanism and linkages for producing relative movement between the jaws and the outer tubular member. Because the jaws are carried at the end of a tubular body, the forceps unit can be positioned within an anatomical cavity with various inner members being advanced distally through the tubular body for performing different functions. The inner members of the operating unit carry instruments or operating members such as single-edge cutting blades, scissors, biopsy containers, cauteries, solid and hollow needles, ligatures, hooks and/or endoscopes, for example, and are easily removed from the tubular member of the forceps unit for replacement by other inner members without removing the forceps unit from the anatomical cavity. The inner members can also have hollow tubular shafts open at a distal end for facilitating visualization with a conventional endoscope, illumination with fiber optics or other suitable light sources, for passage of implements such as blades or ligature appliers to cooperate with instruments mounted at the distal end of the inner member tubular shaft, and/or for introducing or collecting fluids prior to, during or after an operative step, such as cutting or puncturing, is completed. When a tubular shaft is closed at a distal end and a hollow needle or hook extends from an opening in the closed distal end, the inner member can be used for precisely administering medicaments such as vasoconstrictors (e.g., epinephrine) or other fluids to an operative site, or for passing lengths of suture material through the hollow needle or hook to suture tissue within the anatomical cavity.

The operating unit inner member can be biased proximally within a hub configured to mount the forceps unit housing in a releasable manner, can be fixed to such a hub, or can be inserted directly into the housing for being advanced distally through the forceps unit. If biased within a hub, the inner member is advanced into the intermediate member carrying the jaws by threadedly or otherwise engaging the hub to the housing and is positioned between the jaws by distal movement of a handle mounted at the proximal end of the inner member outside the anatomical cavity. Any locking mechanism, including levers, spring-biased detents or a lost-motion coupling, can be used for locking the inner member flange at locations at or between the proximal and distal ends of the hub. If fixed, the inner member is advanced between the jaws simply by mounting the hub to the housing. The forceps unit housing and operating unit hub can have any configuration for being releasably coupled including threaded or telescoping portions, detents, latches or any other type of suitable connection. The housing and hub can be cylindrical or rectangular as shown or have any other configuration in cross-section.

Jaws 18 and 20 of the present invention can be straight, curved and/or angled and can have integrally formed or removable inserts with configurations for grasping and holding tissue and objects such as needles. The inserts can have any combination or number of longitudinal grooves formed in the inserts for accommodating operating members such as blades, scissors, biopsy tools, needles, hooks, surgical clips or any other types of medical implements. The grooves can extend part way to define stops or abutments limiting distal movement of the operating members or can extend the complete length of the inserts to form openings or apertures at a distal end of the jaws to allow passage of the operating members beyond the distal end of the jaws when the jaws are closed. The jaws can have any shape in cross-section when closed, including circular, elliptical, rectangular and polygonal configurations, and can have opposed arcuate or concave portions for clamping tubular objects without compressing the objects. Integral blades can be carried by one or both jaws and centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together. Furthermore, any blade of a scissor device carried by the jaws or an inner member of the present invention can be provided with a sharp hook extending transversely from the distal end of the blade in opposed relation to the other blade.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of electrical connector 92 opposite handle 90 on operating unit 13 is merely exemplary of the many various locations at which an electrical connector can be positioned. For example, an electrical connection could be made directly with the intermediate member flange through the housing of the forceps unit to utilize the forceps jaws as conductive elements for performing electrosurgery. Also, inner surfaces of any of the tubular members, such as tubular members 54 and/or 74, can be electrically insulated to permit passage of electrosurgical instruments therethrough as a backup.

The handles and linkages shown and described herein for sliding the outer member over the jaws are exemplary of the types of conventional handle mechanisms suitable for performing the function of closing the jaws; accordingly, the handles can have any configuration for producing relative movement between the outer and intermediate members, including two pivoted legs with finger loops and sliding brackets as shown, one fixed and one pivoted leg with finger loops, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired. Suitable linkages include brackets with sliding motion, gears mounted on or between handles and the outer and intermediate members, pulleys and cords or any other direct or indirect coupling mechanisms. The intermediate and outer members can be frictionally fitted to maintain a current position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for releasing the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost. The forceps unit and/or operating unit can have various Valves, stop cocks and seals to control fluid flow therethrough, such as the valve 362 shown in FIG. 63 or the valve shown schematically in phantom in FIG. 2 at 58, and conventional detent mechanisms can be used to connect or latch the hub with the housing when the forceps unit and the operating unit are assembled.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscopic instrument comprising
   a housing;
   an outer tubular member having a proximal end mounted by said housing and terminating distally at a distal end;
   an intermediate member having a tubular body disposed telescopically within said outer tubular member, a proximal end mounted by said housing and an integral one-piece distal end defining a pair of opposed jaws resiliently biased apart;
   an inner member removably disposed at least partly within said intermediate member and carrying an operating member; and
   handle means coupled with at least one of said intermediate and outer tubular members for creating relative movement between said intermediate and outer tubular members, whereby said pair of opposed jaws is closed when said distal end of said outer tubular member is advanced distally over said jaws.

2. An endoscopic instrument as recited in claim 1 wherein said jaws define opposed grasping surfaces.

3. An endoscopic instrument as recited in claim 2 wherein a longitudinal groove is formed in one of said opposed grasping surfaces.

4. An endoscopic instrument as recited in claim 3 wherein said longitudinal groove extends part way along said grasping surface to define a stop limiting distal movement of an operating member advanced along said groove.

5. An endoscopic instrument as recited in claim 3 wherein said longitudinal groove extends along an entire length of said grasping surface to define an aperture at a distal end of said jaw.

6. An endoscopic instrument as recited in claim 2 wherein a longitudinal groove is formed in each of said opposed grasping surfaces.

7. An endoscopic instrument as recited in claim 6 wherein said longitudinal grooves extend part way along said grasping surfaces to define a pair of stops limiting distal movement of an operating member advanced along said grooves.

8. An endoscopic instrument as recited in claim 6 wherein said longitudinal grooves extend along entire lengths of said grasping surfaces to define an aperture at a distal end of said jaws.

9. An endoscopic instrument as recited in claim 2 wherein at least one of said grasping surfaces carries a cutting blade.

10. An endoscopic instrument as recited in claim 9 wherein one of said grasping surfaces carries a cutting blade and a pocket formed in said opposed grasping surface for receiving said cutting blade.

11. An endoscopic instrument as recited in claim 9 wherein said opposed grasping surfaces carry opposed cutting blades.

12. An endoscopic instrument as recited in claim 11 wherein said cutting blades are arranged to slidingly contact when said jaws are closed and pockets are formed in said grasping surfaces alongside said cutting blades for receiving said opposed cutting blade.

13. An endoscopic instrument as recited in claim 9 wherein a groove is formed in at least one of said grasping surfaces and said cutting blade is laterally offset from said groove.

14. An endoscopic instrument as recited in claim 1 and further comprising cam members carried on outer surfaces of said jaws.

15. An endoscopic instrument as recited in claim 1 wherein said jaws include opposed arcuate portions defining an opening between said jaws.

16. An endoscopic instrument as recited in claim 1 wherein one of said jaws is fixed parallel to a longitudinal axis of said intermediate member and the other of said jaws is movable.

17. An endoscopic instrument as recited in claim 1 wherein said operating member includes a blade with a distal cutting edge.

18. An endoscopic instrument as recited in claim 17 wherein said inner member includes a tubular shaft having an open distal end and said blade is disposed diametrically across said open distal end of said tubular shaft.

19. An endoscopic instrument as recited in claim 18 wherein a longitudinal groove is formed in at least one jaw and said blade is arranged to slide along said groove when moved between said jaws.

20. An endoscopic instrument as recited in claim 1 wherein said operating member includes a pair of pivoted blades with opposed cutting edges.

21. An endoscopic instrument as recited in claim 20 wherein one of said blades is fixed to extend longitudinally and the other of said blades is movable.

22. An endoscopic instrument as recited in claim 20 wherein both blades are movable.

23. An endoscopic instrument as recited in claim 20 wherein a pair of opposed grooves are formed in said jaws and said blades are biased apart to fit within said grooves when advanced between said jaws.

24. An endoscopic instrument as recited in claim 1 wherein said operating member includes a pair of opposed biopsy boxes.

25. An endoscopic instrument as recited in claim 24 wherein one of said biopsy boxes is fixed to extend longitudinally and the other of said biopsy boxes is movable.

26. An endoscopic instrument as recited in claim 24 wherein both of said biopsy boxes are movable.

27. An endoscopic instrument as recited in claim 24 wherein a pair of opposed grooves are formed in said jaws and said biopsy boxes are biased apart to fit within said grooves when advanced between said jaws.

28. An endoscopic instrument as recited in claim 1 wherein said inner member includes a tubular shaft and said operating member includes a needle having a tissue penetrating distal end, said needle being carried at a distal end of said tubular shaft.

29. An endoscopic instrument as recited in claim 28 wherein said needle is coaxial with said inner member tubular shaft.

30. An endoscopic instrument as recited in claim 28 wherein said needle is offset from a central longitudinal axis of said inner member tubular shaft.

31. An endoscopic instrument as recited in claim 28 wherein said distal end of said tubular shaft is open and said needle is solid.

32. An endoscopic instrument as recited in claim 28 wherein said distal end of said tubular shaft is closed and said needle is hollow and extends from an opening in said closed distal end of said tubular shaft.

33. An endoscopic instrument as recited in claim 28 wherein said needle is curved.

34. An endoscopic instrument as recited in claim 28 wherein a channel is formed along the length of said needle.

35. An endoscopic instrument as recited in claim 34 and further comprising an implement telescopically fitted within said inner member tubular shaft and carrying a cutting blade at a distal end for sliding along said channel.

36. An endoscopic instrument as recited in claim 28 wherein said needle is angled.

37. An endoscopic instrument as recited in claim 28 wherein a groove is formed in at least one of said jaws and said needle is configured to slide along said groove when said jaws are closed.

38. An endoscopic instrument as recited in claim 1 wherein said inner member includes a tubular shaft and said operating member includes a hook.

39. An endoscopic instrument as recited in claim 38 wherein said hook includes a shank coaxial with said inner member tubular shaft.

40. An endoscopic instrument as recited in claim 38 wherein said hook includes a shank offset from a central longitudinal axis of said inner member tubular shaft.

41. An endoscopic instrument as recited in claim 38 wherein a distal end of said tubular shaft is open and said hook is solid.

42. An endoscopic instrument as recited in claim 38 wherein a distal end of said tubular shaft is closed and said hook is hollow and extends from an opening in said closed distal end of said tubular shaft.

43. An endoscopic instrument as recited in claim 38 wherein a channel is formed along an inner edge of said hook.

44. An endoscopic instrument as recited in claim 43 and further comprising an implement telescopically fitted within said inner member tubular shaft and carrying a cutting blade at a distal end for sliding along said channel.

45. An endoscopic instrument as recited in claim 44 wherein said cutting blade has a curved distal cutting edge configured to conform to the shape of said hook.

46. An endoscopic instrument as recited in claim 38 wherein said hook is angled.

47. An endoscopic instrument as recited in claim 38 wherein a groove is formed in at least one of said jaws and said hook is configured to slide along said groove when said jaws are closed.

48. An endoscopic instrument as recited in claim 1 and further comprising a hub configured to be releasably coupled-with said housing and to carry said inner member.

49. An endoscopic instrument as recited in claim 48 wherein said inner member is biased proximally relative to said hub and further comprising a handle mounted on said inner member externally of said hub for being advanced distally.

50. An endoscopic instrument as recited in claim 49 and further comprising safety means for locking the inner member to prevent movement relative to said hub.

51. An endoscopic instrument as recited in claim 1 wherein said inner member includes valve means at a proximal end for controlling passage through said inner member.

52. An endoscopic instrument comprising a housing;

an outer tubular member having a proximal end mounted by said housing and terminating distally at a distal end;

an intermediate member having a tubular body disposed telescopically within said outer tubular member, a proximal end mounted by said housing and an integral one-piece distal end defining a pair of opposed jaws resiliently biased apart, said intermediate member defining a lumen in communication with an opening in said housing;

bias means for biasing said outer tubular member over said jaws; and handle means coupled with at least one of said intermediate and outer tubular members for creating relative movement between said intermediate and outer tubular members, whereby said pair of opposed jaws can be opened when said distal end of said outer tubular member is retracted proximally relative to said jaws.

53. A method of performing endoscopic procedures comprising the steps of introducing a tubular member with integrally formed jaws through an opening in an anatomical cavity wall;

grasping anatomical tissue with the jaws;

advancing an inner member distally through the tubular member; and performing a medical procedure with the inner member.

54. A method as recited in claim 53 wherein said performing step includes the step of using an operating member carried at a distal end of the inner member to perform at least one of the functions of cutting, cauterizing, penetrating, injecting, grasping, manipulating, hooking, collecting a biopsy, creating suction, dissecting, irrigating and aspirating.

55. A method as recited in claim 53 wherein said introducing step includes closing the forceps jaws by sliding an outer tubular member over the jaws.

56. A method as recited in claim 55 wherein said grasping step includes sliding the outer tubular member off of the jaws to permit the jaws to resiliently separate, positioning the anatomical tissue between the separated jaws and sliding the outer tubular member over the jaws to close the jaws around the anatomical tissue.

57. A method of performing endoscopic procedures comprising the steps of introducing a tubular member with integrally formed jaws through an opening in an anatomical cavity wall;

advancing an inner member carrying an operating member distally through the tubular member until the operating member protrudes distally from the jaws; and performing a medical procedure with the operating member.

58. A method as recited in claim 57 wherein said performing step includes using the operating member to perform at least one of the functions of cutting, cauterizing, penetrating, injecting, hooking, grasping, dissecting, manipulating, collecting a biopsy, creating suction, irrigating and aspirating.

59. A method as recited in claim 57 wherein said introducing step includes closing the forceps jaws by sliding an outer tubular member over the jaws and said advancing step includes moving a cutting blade along a groove formed in the jaws.

60. A method as recited in claim 57 wherein said introducing step includes closing the forceps jaws by sliding an outer tubular member over the jaws and said advancing step includes the step of moving a needle along a groove formed in the jaws.

61. A method as recited in claim 57 wherein said introducing step includes closing the forceps jaws by sliding an outer tubular member over the jaws and said advancing step includes moving a hook along a groove formed in the jaws.

62. A method as recited in claim 61 and further comprising the steps of maintaining the jaws in a closed condition, positioning anatomical tissue between the hook and the closed jaws and retracting the hook in a proximal direction to hold the anatomical tissue between the hook and the closed jaws.

63. A method as recited in claim 62 and further comprising the step of advancing a cutting blade through the inner member to slide along a channel formed in the hook and cutting the anatomical tissue held between the hook and the closed jaws.

64. A method of performing endoscopic procedures comprising the steps of introducing a tubular member with integrally formed jaws through an opening in an anatomical cavity wall;

advancing an inner member distally through the tubular member until an operating member carried by the inner member is disposed between the jaws, said operating member having opposed distal portions biased apart;

opening the jaws to permit the opposed distal portions of the operating member to separate;

positioning anatomical tissue between the opposed distal portions of the operating member; and closing the jaws to move the opposed distal portions of the operating member toward one another.

65. A method as recited in claim 64 wherein said advancing step includes positioning an operating member having a pair of pivoted blades with opposed cutting edges between the jaws.

66. A method as recited in claim 64 wherein said advancing step includes positioning an operating member having a pair of opposed biopsy boxes between the jaws.

* * * * *